United States Patent [19]

Iijima et al.

[11] Patent Number: 4,543,323

[45] Date of Patent: Sep. 24, 1985

[54] LIGHT-SENSITIVE SILVER HALIDE PHOTOGRAPHIC MATERIAL

[75] Inventors: Toshifumi Iijima; Satoshi Nakagawa; Hiroshi Menjo, all of Hino, Japan

[73] Assignee: Konishiroku Photo Industry Co., Ltd., Tokyo, Japan

[21] Appl. No.: 560,148

[22] Filed: Dec. 12, 1983

[30] Foreign Application Priority Data

Dec. 18, 1982 [JP] Japan ................................ 57-223495
Dec. 20, 1982 [JP] Japan ................................ 57-221966

[51] Int. Cl.$^4$ ............................................. G03C 1/46
[52] U.S. Cl. .................................... 430/503; 430/504; 430/505; 430/506; 430/509; 430/553; 430/555; 430/557; 430/558; 430/955
[58] Field of Search ............... 430/503, 504, 505, 506, 430/509, 955, 557, 553, 555, 558

[56] References Cited

U.S. PATENT DOCUMENTS

| | | | |
|---|---|---|---|
| 4,145,219 | 3/1979 | Kato et al. | 430/502 |
| 4,414,308 | 11/1983 | Hamada | 430/505 |
| 4,420,556 | 12/1983 | Booms et al. | 430/549 |
| 4,438,194 | 3/1984 | Hamada | 430/506 |

*Primary Examiner*—J. Travis Brown
*Attorney, Agent, or Firm*—Frishauf, Holtz, Goodman & Woodward

[57] ABSTRACT

There is disclosed a light-sensitive silver halide photographic material having at least one light-sensitive layer constituted of a plural number of silver halide emulsions provided on a support, and a non-light-sensitive intermediate layer containing a diffusion resistant coupler capable of forming a migratable color forming dye or a compound capable of forming a flow-out type coupling product provided at least adjacent to the silver halide emulsion layer with the highest light sensitivity among the plural number of silver halide emulsion layers on its support side.

The light-sensitive material according to this invention exhibits excellent photographic characteristics such as sensitivity, graininess, sharpness, storability and gradation.

21 Claims, No Drawings

LIGHT-SENSITIVE SILVER HALIDE PHOTOGRAPHIC MATERIAL

BACKGROUND OF THE INVENTION

This invention relates to a light-sensitive silver halide photographic material, more particularly to a light-sensitive silver halide photographic material improved in photographic characteristics such as sensitivity, graininess, sharpness, storability and gradation.

Heretofore, as the light-sensitive silver halide photographic material (hereinafter abbreviated as light-sensitive material), development of a light-sensitive material having high sensitivity and finely micropulverized grains has been desired, and a number of improved light-sensitive materials, particularly color light-sensitive materials, have been proposed.

As one of the light-sensitive materials suited for the above object, for example, U.K. Pat. No. 923,045 states that sensitivity can be enhanced without deterioration by applying the same color sensitive silver halide emulsion in separated layers in a high sensitivity silver halide emulsion layer (hereinafter called as high sensitivity emulsion layer) and a low sensitivity silver halide emulsion layer (hereinafter called as low sensitivity emulsion layer) and further by controlling the maximum color forming density at a low level.

In recent years, however, particularly the color light-sensitive material for photography is required progressively to be higher in sensitivity, whereby it is obliged to use coarse silver halide inferior in graininess and/or a coupler with greater coupling speed in the silver halide emulsion layer. For this reason, in the method described in the above U.K. Pat. No. 923,045, the degree of improvement became insufficient, and further elaborations have been done for improvement of graininess.

For example, in Japanese Patent Publication No. 15495/1974, the graininess is stated to be improved by provision of a gelatin layer between the high sensitivity emulsion layer and the low sensitivity emulsion layer. In this method, while graininess at lower density regions can be improved, bad influences on gradation are markedly observed. On the other hand, for restoration of gradation, if sensitivity of the low sensitivity emulsion layer enhanced according to the prior art, for example, by increasing the grain size of silver halide, the graininess in the medium density region which is important particularly in practical technique will unfavorably be deteriorated. Further, in the multi-layer color light-sensitive material having the above constitution, there is also involved the drawback that the color formed image density will be deteriorated in its stability depending on the changes in the developing processing conditions such as pH value, temperature and time.

As another example, Japanese Provisional Patent Publication No. 155536/1982 states that both graininess and gradation can be improved by providing a non-light-sensitive hydrophilic colloid layer between the high sensitivity emulsion layer and the low sensitivity emulsion layer, containing a diffusion resistant coupler for photography which is color formed to substantially the same hue as the diffusion resistant coupler for photography contained in the high sensitivity and low sensitivity emulsion layers, and has a coupling speed not greater than that of the diffusion resistant coupler for photography contained in the high sensitivity emulsion layer. This method involves no failure in gradation and is improved in graininess, but it is not yet satisfactory in improvement in graininess at the regions from low density to medium density. For example, in the above Japanese Patent Publication No. 15495/1974 and Japanese Provisional Patent Publication No. 7230/1978, there is described a method in which a medium sensitivity emulsion layer is provided between the high sensitivity emulsion layer and the low sensitivity emulsion layer and a compound capable of releasing a diffusive developing inhibiting compound (hereinafter called as DIR compound) through the reaction with the oxidized product of a color developing agent is incorporated in said layer. However, these methods have the drawbacks of increased fog accompanying the increased amount of silver halide as well as increase in amounts of valuable silver resources.

Also, in a light-sensitive material having two or more layers of silver halide emulsion layers sensitive to the same color, it is a general practice to improve graininess by making the silver halide emulsion layer having higher sensitivity lower in coupler density (in this case, it appears that the oxidized product of a developing agent formed in the developing reaction will be diffused in a wide scope searching for partners for coupling reaction, thereby forming an unfocused dye cloud with low density without worsening graininess). However, the oxidized product of the developing agent formed by development of the silver halide in said silver halide emulsion layer having higher light sensitivity does not exist only within the layer formed, but will be diffused even to the siler halide emulsion layer having lower light sensitivity to form a dye cloud with conspicuous graininess therein. As the result, when viewing the light-sensitive material, the influence of the developed silver grains in the silver halide emulsion having higher sensitivity will reach even the density (or light-sensitive) region under question, thus ensuing the problem of deterioation of graininess.

Accordingly, an object of this invention is to provide a light-sensitive material having high sensitivity as well as good gradation, further improved in sharpness, image storability and graininess, requiring only a small amount of silver to be employed.

SUMMARY OF THE INVENTION

As the result of various studies made by the present inventors, it has been found that the above object can be accomplished by a light-sensitive silver halide photographic material having at least one light-sensitive layer constituted of a plural number of silver halide emulsions which are substantially the same in color sensitiveness but different in light sensitivity and containing a diffusion resistant coupler for photography capable of forming a diffusion resistant color forming dye through the reaction with the oxidized product of a color developing agent provided on a support, which comprises a non-light-sensitive intermediate layer provided at least adjacent to the silver halide emulsion layer with the highest light sensitivity among said plural number of silver halide emulsion layers on its support side, said non-light-sensitive intermediate layer containing a diffusion resistant coupler capable of forming a mobile color forming dye which can be color formed to substantially the same hue as the said diffusion resistant color forming dye through the coupling reaction with the oxidized product of a color developing agent or a compound capable of forming a flow-out type coupling product through the coupling reaction with the oxidized product of a color developing agent.

In short, this invention proposes a novel improved light-sensitive material as a trial for overcoming the above-mentioned task.

DESCRIPTION OF THE PREFERRED EMBODIMENTS

This invention is to be described in detail below by referring primarily to one embodiment of this invention. For example, in this invention, the light-sensitive material comprises light-sensitive layers different in light sensitivity, namely a high sensitivity emulsion layer and a low sensitivity emulsion layer with an intermediate layer according to this invention therebetween.

In this case, each of the high sensitivity emulsion layer and the low sensitivity emulsion may be constituted of one layer, or preferably two or more layers, since the effect of the method described in U.K. Pat. No. 923,045 as cited above can additively be added further to the effect of this invention. Also, in this invention it is preferable to provide the high sensitivity layer region apart farther from the support than the low sensitivity emulsion layer, and when each of the high sensitivity emulsion layer and the low sensitivity emulsion layer is constituted of two or more layers, it is preferable to provide a layer with lower sensitivity nearer to the support.

The sensitivity difference between the high sensitivity emulsion layer and the low sensitivity emulsion layer may be determined optimally according to the known method with considerations about gradation and graininess, but may preferably be approximately 0.1 to 1.0 log E (E: dosage of exposure).

Further, the high sensitivity emulsion layer and the low sensitivity emulsion layer have substantially the same color sensitiveness, and after the color developing processing, both of the emulsion layers should preferably contain diffusion resistant couplers for photography capable of forming color forming dyes having substantially the same hue. In this case, it is preferred that the contents of the diffusion resistant couplers for photography contained in the respective high sensitivity and low sensitivity emulsion layers should be such that the color forming density of the color forming dye formed as the result of the coupling reaction with the oxidized product of a color developing agent is higher in the low sensitivity emulsion layer than in the high sensitivity emulsion layer.

It is also possible to incorporate in the intermediate layer according to this invention the diffusion resistant coupler for photography to be contained in both of the emulsion layers.

The intermediate layer according to this invention should be provided by coating at a dry film thickness, ranging preferably from $0.2\mu$ to $2.0\mu$.

And, the intermediate layer according to this invention contains a diffusion resistant coupler capable of forming a mobile color forming dye which can be color formed to substantially the same hue as the said diffusion resistant color forming dye through the coupling reaction with the oxidized product of a color developing agent or a compound capable of forming a flow-out type coupling product through the coupling reaction with the oxidized product of a color developing agent.

Now, the diffusion resistant coupler according to this invention will be explained in the following:

The term "diffusion resistant" herein used has a meaning ordinarily applied in light-sensitive materials, and for all practical purposes, it means the property such that the coupler will not be moved or drifted through an organic colloid layer such as gelatin layer, when the light-sensitive layer of this invention is treated in an alkali atmosphere, preferably in a medium of pH 10 or higher.

The coupler of this invention has a ballast group at the coupling position which immobilizes the coupler to make it diffusion resistant, and also a control group at the non-coupling position for controlling the mobility of the color forming dye formed by the coupling reaction with the oxidized product of a color developing agent. When the coupler couples with the oxidized product of a color developing agent, the ballast group will be eliminated, whereby the color forming dye formed becomes mobile.

The "mobility" of "the diffusion resistant coupler capable of forming a mobile color forming dye" according to this invention means a mobility to the extent that the color forming dye formed by the coupling reaction with the oxidized product of a color developing agent can be moved within the layer containing the diffusion resistant coupler. Such a mobility can be controlled by the above-mentioned control group of the coupler. The control group depends on the coupler mother nucleus to which this groups is bonded, other substituents introduced into the coupler and the color developing agent employed.

The light-sensitive material of this invention, as described above, has at least one light-sensitive layer constituted of a plural number of silver halide emulsions which are substantially the same in color sensitiveness but different in light sensitivity and containing a diffusion resistant coupler for photography capable of forming a diffusion resistant color forming dye through the reaction with the oxidized product of a color developing agent provided on a support, and further a non-light-sensitive intermediate layer is provided at least adjacent to the silver halide emulsion layer with the highest light sensitivity among said plural number of silver halide emulsion layers on its support side, and further said non-light-sensitive intermediate layer contains a diffusion resistant coupler capable of forming a migratable color forming dye which can be color formed to substantially the same hue as the said diffusion resistant color forming dye through the coupling reaction with the oxidized product of a color developing agent.

The effect of this invention can be exhibited by such a light-sensitive material, and this effect, although not clearly understood, may be considered to be due to the fact that deterioration of sharpness and graininess in the adjacent silver halide emulsion layer with lower sensitivity caused by the oxidized product of a color developing agent formed excessively in the silver halide emulsion having the highest sensitivity during color development of the light-sensitive material after exposure can be prevented and also gradation can be controlled, and further at the same time due to marked improvement of graininess at leg portion by formation of a mobile color forming dye within the intermediate layer according to this invention through the coupling reaction of the "diffusion resistant coupler capable of forming a mobile color forming dye" according to this invention with the oxidized product of a color developing agent.

The diffusion resistant coupler capable of forming a mobile color forming dye according to this invention as mentioned above may be represented by the following formula [I]:

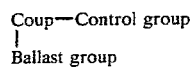   [I]

wherein Coup is a coupler mother nucleus capable of forming a color forming dye through the coupling reaction with the oxidized product of a color developing agent; Ballast group is a group which is bonded to the coupling position of said coupler and can be eliminated from Coup during the coupling reaction between said coupler and the oxidized product of a color developing agent, said Ballast group having a size and a shape of molecule enough to make the coupler non-diffusive; and Control group is a group bonded to Coup at the non-coupling position for controlling the color forming dye formed through the coupling reaction between the coupler and the oxidized product of a color developing agent so that it may be mobile.

The above Coup, which represents a coupler mother nucleus, may be any of the coupler mother nuclei which is known or used in this field of the art for forming a color forming dye by the coupling reaction with the oxidized product of a color developing agent.

For example, as the yellow couplers, there may be employed benzoylacetanilide type yellow couplers or pivaloylacetanilide type yellow couplers as disclosed in U.S. Pat. Nos. 2,298,448, 2,407,210, 2,875,057, 3,408,194, 3,265,506 and 3,447,928; and "Farb-Kuppler-eine-Literaturubersicht" Agfa Mitteilung, Vol. 2, pp. 112-126, 1961. As for magenta couplers, it is possible to use various kinds of magenta couplers such as pyrazolone type magenta couplers, indazolone type magenta couplers, pyrazolotriazole type magenta couplers and pyrazolobenzimidazole type magenta couplers as disclosed in U.S. Pat. Nos. 2,369,489, 2,343,703, 2,311,082, 2,600,788, 2,908,573, 3,152,896 and 3,519,429 and the report of Agfa AG. as cited above, pp. 126-156. Further, in the case of cyan couplers, naphthol type or phenol type couplers, as disclosed in U.S. Pat. Nos. 2,367,531, 2,433,730, 2,474,293, 2,772,162, 2,895,826, 3,002,836, 3,034,892 and 3,041,236; and the report of Agfa AG. as cited above, pp. 156-175, may be used.

Next, the ballast group indicated in the formula [I] has a size and a shape of molecule enough to make the coupler non diffusive. Useful ballast groups of this kind are groups having an alkyl moiety or an aryl moiety with 8 or more carbon atoms, preferably 8 to 32 carbon atoms, said alkyl moiety and aryl moiety being bonded at the coupling position to the coupler mother nucleus directly or through a connecting group [e.g. —O—, —S—, —N=N—,

(wherein Z is a group of atoms necessary for forming a 5- to 7-membered heterocyclic ring)]. Preferably, the ballast group may be one bonded through a connecting group, such as alkoxy, aryloxy, alkylthio, arylthio and nitrogen-containing heterocyclic ring.

The control group in this invention is a group having a size and a shape of molecule suitable for imparting mobility to the color forming dye formed as described above.

As the group suitable for imparting mobility to the color forming dye as described above, it is preferred to use an alkyl group having 1 to 20 carbon atoms and an aryl group having 6 to 20 atoms. These groups may also be substituted with a group for changing the spectral characteristics or mobility of the color forming dye. These control groups may also have connecting groups for bonding said control group to the coupler mother nucleus. Such connecting groups may include, for example, —O—, —S—, —CO—, —COO—, —NR—, —CONR—, —NRCO—, —SO₂NR—, —NRSO₂—, —NRCONR— (wherein R is a hydrogen atom, an alkyl group or an aryl group) and the like.

Of the diffusion resistant couplers for forming mobile color forming dyes in this invention, the couplers preferable as the yellow coupler may be represented by the following formula [II]:

[Yellow coupler]

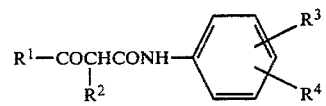   [II]

wherein $R^1$ is an aryl group (e.g. a phenyl group) or an alkyl group (e.g. a tertiary alkyl group such as t-butyl); $R^2$ is the ballast group as defined above; $R^3$ is the control group as defined above; and $R^4$ is a hydrogen atom, a halogen atom, an alkyl group, an alkoxy group or the control group as defined above.

Next, preferable cyan couplers may be represented by the following formulae [III] and [IV]:

[Cyan couplers]

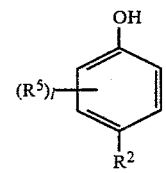   [III]

and

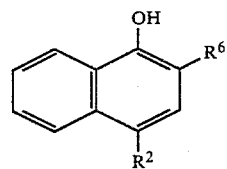   [IV]

In the formulae [III] and [IV], $R^2$ has the same meaning as defined in the formula [II]; at least one of $R^5$ is the control group as defined above, and the remainder representing either identical or different hydrogen atoms, halogen atoms, alkyl groups, alkoxy groups, alkylamino groups or acylamide groups; l is an integer of 1 to 3, preferably 3; and $R^6$ represents the control group as defined above.

Further, preferably magenta couplers can be represented by the following formulae [V] and [VI]:

[Magenta couplers]

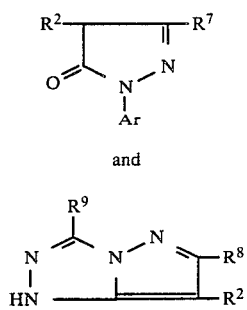

In the formulae [V] and [VI], $R^2$ is the same as defined defined above; $R^7$ is the control group as defined above; Ar is a phenyl group which may have at least one of a substituent selected from the group of a halogen atom, an alkyl group, an alkoxy group and an amino group, and said phenyl group may have the control group; one of $R^8$ and $R^9$ represents the control group and the other represents a hydrogen atom, halogen atom, alkyl group, alkoxy group, aryl group, amino group or acylamide group.

In the above couplers, unless otherwise specifically noted, the alkyl group, the alkoxy group and the alkylamide group each contains 1 to 8 carbon atoms, the aryl group contains 6 to 10 carbon atoms, and the amino group is inclusive of primary, secondary and tertiary amino groups. These substituents and ballast groups also include those substitued with the groups such as halogen atom, hydroxy, carboxy, amino, amide, carbamoyl, sulfamoyl, sulfonamide, alkyl, alkoxy and aryl.

In the following, typical specific examples of the diffusion resistant couplers capable of forming mobile color forming dyes in this invention are enumerated, but this invention is not lilmited thereto.

(Example compounds)

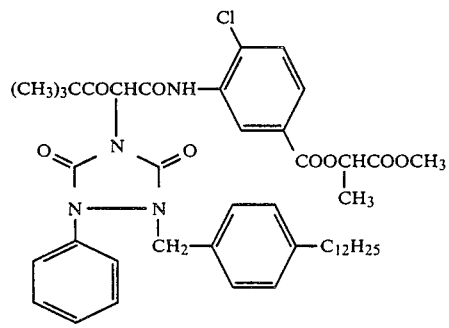

[I-1]

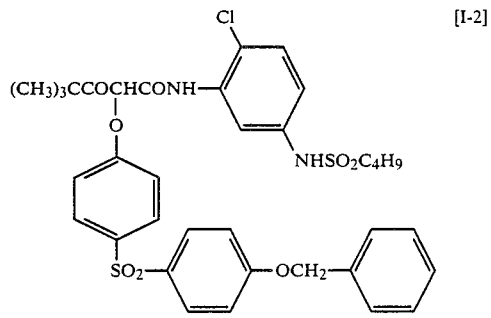

[I-2]

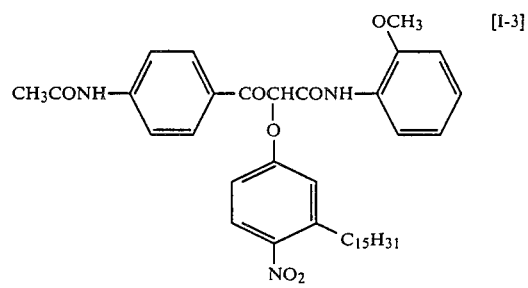

[I-3]

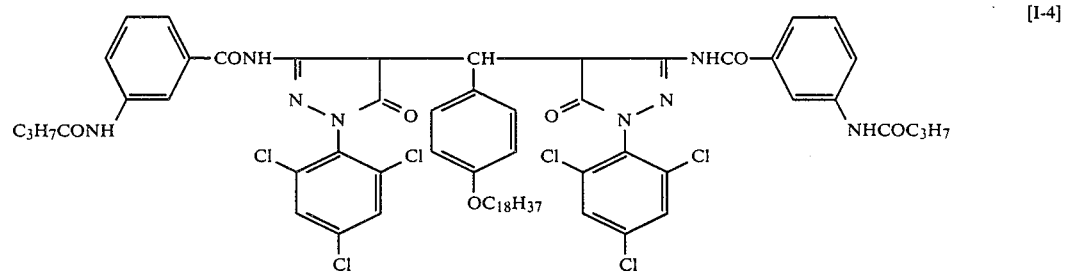

[I-4]

-continued
(Example compounds)
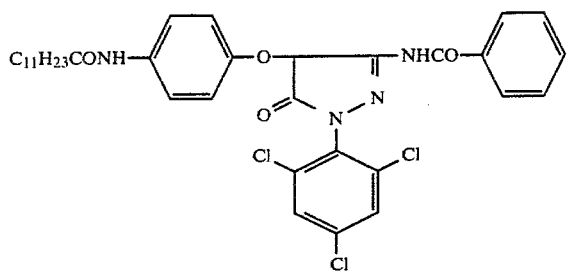 [I-5]
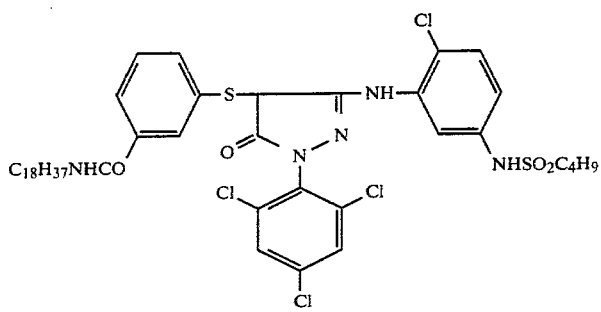 [I-6]
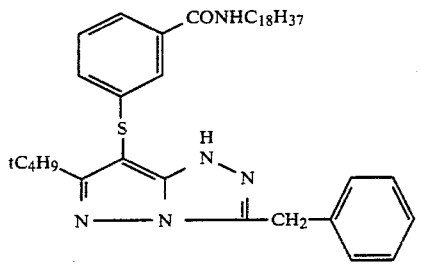 [I-7]
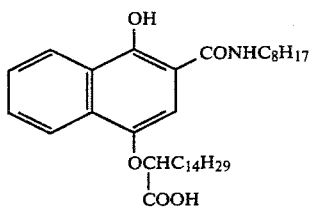 [I-8]
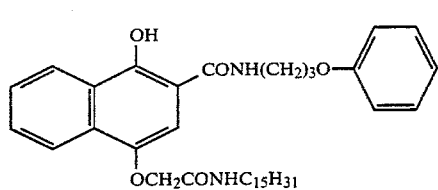 [I-9]
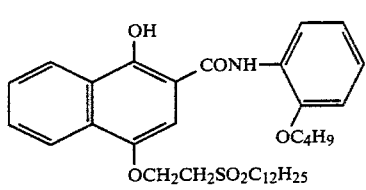 [I-10]
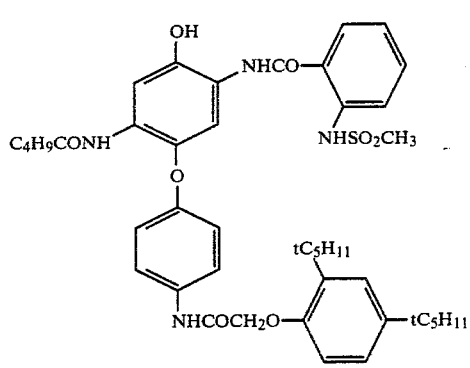 [I-11]
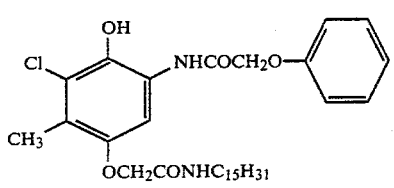 [I-12]

-continued
(Example compounds)

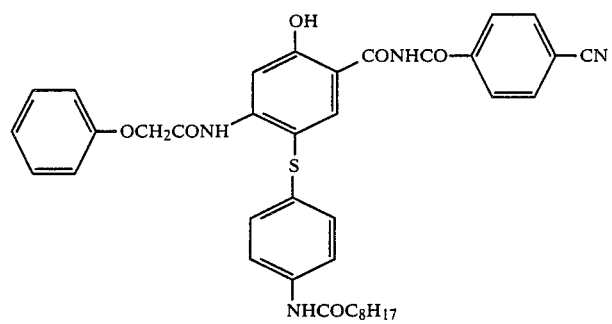

[I-13]

Having thus enumerated specific examples of the couplers of this invention, the couplers, including both of those as enumerated above and other couplers of this invention, may be used either singly or as a combination of two or more kinds.

In the following, representative synthesis examples about these couplers according to this invention are described, but other couplers can also easily be synthesized according to the procedures similar to these synthetic methods.

SYNTHESIS EXAMPLE 1
(Synthesis of example compound [I-1])

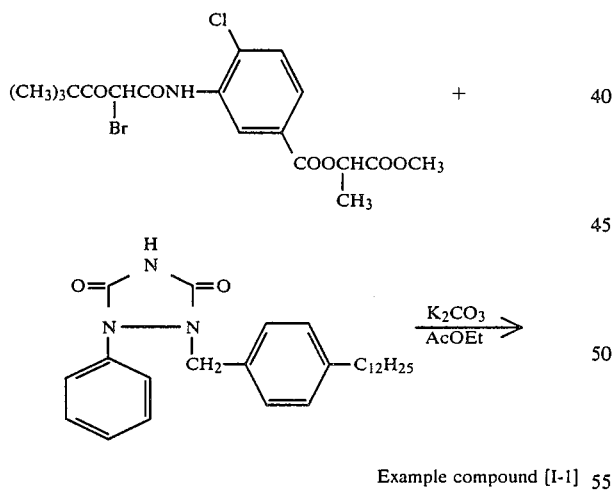

Example compound [I-1]

To a solution of 8.2 g of α-pivaloyl-α-bromo-2-chloro-5-(2-methoxycarbonyl)ethoxycarbonyl-acetanilide and 8.7 g of 3-phenyl-4-(4-dodecylbenzyl)urazole dissolved in 100 ml of ethyl acetate, 1.4 g of anhydrous potassium carbonate was added and the mixture was refluxed for 5 hours. The reaction mixture was washed with addition of 200 ml of water, then dried over magnesium sulfate, followed by evaporation of ethyl acetate under reduced pressure. The oily product obtained was dissolved by heating in 10 ml of n-hexane, and left to stand, whereby white powdery crystals were precipitated. Yield: 10.7 g.

SYNTHESIS EXAMPLE 2
(Synthesis of example compound [I-6])

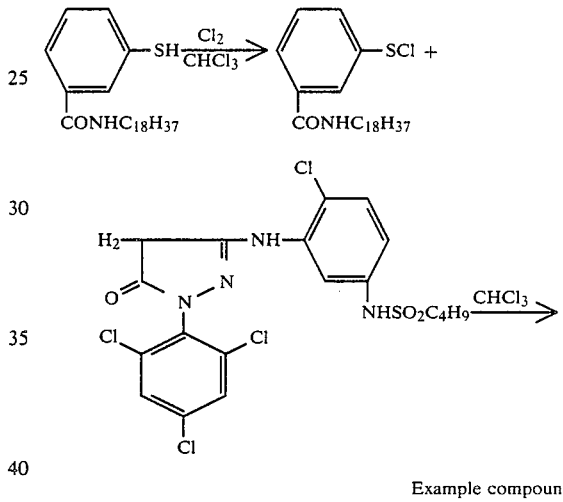

Example compound [I-6]

To 50 ml of chloroform was added 6.5 g of 3-octadecylcarbamoylthiophenol, and under room temperature chlorine gas was passed through the mixture for 30 minutes to obtain a yellow solution. The chloroform was evaporated under reduced pressure to give sulphenyl chloride as an yellow oily product. The sulphenyl chloride was dissolved without purification in 100 ml of chloroform, and 7.4 g of 1-(2,4,6-trichlorophenyl)-3-(2-chloro-5-butanesulfonamido)aniline-5-pyrazolone, followed by refluxing for 2 hours. Then, chloroform was evaporated under reduced pressure, and the residue obtained was chromatographed on a silica gel column with a solvent mixture of n-hexane and ethyl acetate (mixing ratio 2:1) as the eluant, to obtain the title compound.

This was recrystallized from acetonitrile to give pale yellow crystals. Yield: 5.2 g.

The title compound obtained according to the above synthetic method was confirmed to be identical with the example compound by NMR and Mass spectrum.

The coupler of this invention is to be incorporated in the intermediate layer according to this invention which is provided more adjacent to the support side than the silver halide emulsion layer having the highest light sensitivity among the plural number of silver halide emulsion layers with different light sensitivities, as described above. In this case, the amount of the coupler of this invention may generally range from $1\times10^{-7}$ to $8\times10^{-4}$ mole/m$^2$, preferably from $4\times10^{-7}$ to $3\times10^{-4}$ mole/m$^2$. However, the color formed density in the non-sensitive intermediate layer by the amount of the coupler added as specified above should be 0.02 to 0.7, preferably 0.05 to 0.6, particularly 0.05 to 0.2. Here, color fomation of the coupler in the non-sensitive intermediate layer may be considered to be due to the reaction with the oxidized product of a developing agent formed during development of the high sensitivity emulsion layer and the low sensitivity emulsion layer.

Also, in the above-mentioned embodiment, it is also possible to use in combination with the coupler of this invention, a diffusion resistant coupler capable of forming a diffusion resistant color forming dye after the coupling reaction with the oxidized product of a color developing agent in the above intermediate layer. In this case, at least one of said diffusion resistant couplers should preferably have a coupling speed which is equal to or greater than the greatest coupling speed among the diffusion resistant couplers contained in the high sensitivity emulsion layer.

Next, the compound according to this invention will be explained in the following:

The compound according to this invention is capable of forming a flow-out type coupling product through the coupling reaction with the oxidized product of a color developing agent. The "flow-out type" herein mentioned means that the coupling product formed by the coupling reaction of the compound according to this invention with the oxidized product of a color developing agent has mobility within the light-sensitive material during developing processing, namely at the time of color developing processing or thereafter, and is flown out of the system of said light-sensitive material substantially without remaining within said light-sensitive material.

The compound according to this invention, which forms a flow-out type coupling product through the reaction with the oxidized product of a color developing agent as described above, may preferably a compound capable of providing the coupling product which is a color forming dye or colorless.

The compound according to this invention has a ballast group at the coupling site for immobilizing the compound according to this invention and a solubilizing group at the non-coupling site for imparting mobility of the coupling product after the coupling reaction with the oxidized product of a color developing agent. When the coupling occurs with the oxidized product of a color developing agent, the stabilizing group will be eliminated. As the result, the coupling product has mobility.

The compound according to this invention forms a coupling product having mobility through the reaction with the oxidized product of a color developing agent. The mobility in this case may be imparted to the extent as mentioned above such that it may be flown out of the system of the light-sensitive material.

The compound according to this invention can be represented by the following formula [VII]:

wherein COUP is a coupler mother nucleus having a coupling site (asterisk *); BALL is a group which is bonded to the coupling site of COUP and can be eliminated from COUP during the reaction between said COUP and the oxidized product of a color developing agent, said BALL being a Ballast group having a size and a shape enough to make the compound of the formula [VII] diffusion resistant; and SOL is a solubilizing group, which is bonded to COUP at the non-coupling position and imparts mobility to the coupling product formed by coupling between COUP and the oxidized product of a color developing agent so as to be flown out of the system from within the light-sensitive material during or after color developing processing.

As the coupler mother nucleus represented by COUP, there may be included any of coupler mother nuclei, which are known or used in this field for forming a reaction product, having a hue or no color, through the coupling reaction with the oxidized product of a color developing agent. For example, the coupler mother nucleus for forming yellow dye may be acylacetanilide such as acetoacetanilides and benzoylacetanilides; the coupler mother nucleus for forming magenta coupler may be pyrazolones, pyrazolotriazoles, pyrazolobenzimidazoles and indazolones; and the coupler mother nucleus for forming cyan dye may be phenols and naphthols.

BALL is a ballast group having a size and a shape of molecule which will make the compound of the formula [VII] diffusion resistant and it is not particularly limited, so long as it can impart diffusion resistance to the compound of the formula [VII]. Useful groups represented by BALL may include alkyl groups, aryl groups and heterocyclic groups having 8 to 32 carbon atoms. These groups may be either unsubstituted or subsituted. As substituents, there may be included those which will icrease diffusion resistance of the compound of the formula [VII], change the reactivity of the compound of the formula [VII] or undergo coupling reaction to increase diffusibility of BALL after elimination. Further, BALL may preferably be bonded at the coupling site of COUP through a connecting group. Typical connecting groups are oxy (—O—) and thio (—S—).

The solubilizing group represented by SOL is a group for imparting mobility to the coupling product formed by the coupling reaction to the extent such that it can be flown out of the system of the light-sensitive material, as exemplified by ionizable hydroxyl group, carboxyl group, sulfo group and aminosulfonyl group and ionizable salts thereof. One or two or more groups of these groups may be preferably bonded to COUP at the non-coupling sites. Alternatively, there may also advantageously be employed compounds in which solubilizing groups of an appropriate size, such as alkyl groups having 1 to 10 carbon atoms or aryl groups having 6 to 12 groups, which has one or two or more inoizable groups as defined above, are bonded to COUP at the non-coupling sites.

Compounds, in which SOL is bonded to COUP at the non-coupling site through a connecting group, are also preferred. Typical connecting groups may include oxy (—O—), thio (—S—), carbonyl group, carboxyl group, oxycarbonyl group, amino group, carbamoyl group, aminocarbonyl group, ureido group, sulfamoyl group and aminosulfonyl group.

Among the useful solubilizing groups as set forth above, particularly preferable solubilizing groups may include carboxyl group, sulfo group or ionizable salts thereof bonded directly to COUP at the non-coupling site, or alkyl group having 1 to 10 carbon atoms or aryl group having 6 to 12 carbon atoms containing one or two or more carboxyl group, sulfo group or ionizable salts thereof bonded directly or through amino group or carbonyl group to COUP at the non-coupling site.

Further, the compound according to this invention capable of forming yellow, magenta and cyan dyes preferably used in this invention can be represented by the formulae [VIII]–[XII] as shown below.

Of the compounds capable of forming a flow-out type coupling product in this invention, the compounds preferable as the yellow dye forming compound may be represented by the following formula [VIII]:

[Yellow dye forming compounds]

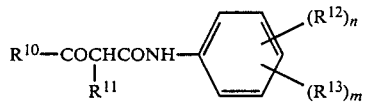

[VIII]

wherein $R^{10}$ is an aryl group (e.g. a phenyl group) or an alkyl group (e.g. a tertiary alkyl group such as t-butyl); $R^{11}$ is the ballast group as defined above (BALL); $R^{12}$ is the control group or the solubilizing group (SOL) as defined above; $R^{13}$ is a hydrogen atom, a halogen atom, an alkyl group or an alkoxy group; and n and m are integers satisfing the relation of $n+m=5$ (provided that each n and m are not zero, and when n and m are 2 or more, the plural groups may be either indentical or different).

Next, preferable cyan dye forming compounds may be represented by the following formulae [IX] and [X]:

[Cyan dye forming compounds]

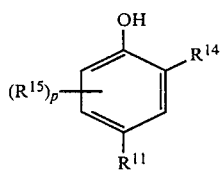

[IX]

and

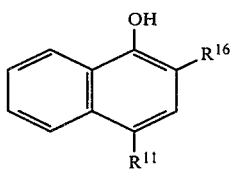

[X]

In the formulae [IX] and [X], $R^{11}$ has the same meaning as defined in the formula [VIII]; at least one of $R^{14}$ and $R^{15}$ is the solubilizing group (SOL) as defined above, the remainder representing either identical or different hydrogen atoms, halogen atoms, alkyl groups, alkoxy groups or alkylamide groups; p is an integer of 1 to 3; and $R^{16}$ represents the solubilizing group (SOL) as defined above.

Further, preferable magneta dye forming compounds can be represented by the following formulae [XI] and [XII]:

[Magenta dye forming compounds]

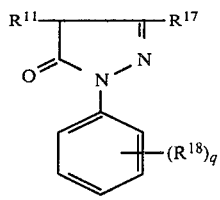

[XI]

and

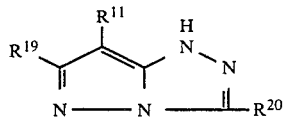

[XII]

In the formulae [XI] and [XII], $R^{11}$ is the same as defined in the formula [VIII]; $R^{17}$ represents the solubilizing group (SOL) as defined above; $R^{18}$ represents a hydrogen atom, a halogen atom, an alkyl group, an alkoxy group or an amino group; q is an integer of 1 to 5 (provided that when q is 2 or more, the plural groups may be either idential or different); and one of $R^{19}$ and $R^{20}$ represents the solubilizing group (SOL) as defined above and the other represents a hydrogen atom, an alkyl group, an alkoxy group, an aryl group or an amino group.

In the above compounds, unless otherwise specifically noted, the alkyl group, the alkoxy group and the alkylamide group each contains 1 to 8 carbon atoms, the aryl group contains 6 to 10 carbon atoms, and the amino group is inclusive of primary, secondary and tertiary amino groups. These substituents and ballast groups (BALL) also include those substitued with the groups such as halogen atom, hydroxy, carboxy, amino, amide, carbamoyl, sulfamoyl, sulfonamide, alkyl, alkoxy and aryl.

In the following, typical specific examples of the compounds according to this invention are enumerated, but these are not limitative of this invention.

(Example compounds)

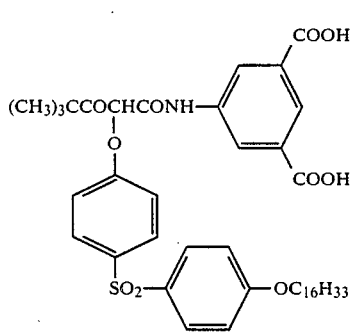

[VII-1]

-continued
(Example compounds)
[VII-2] 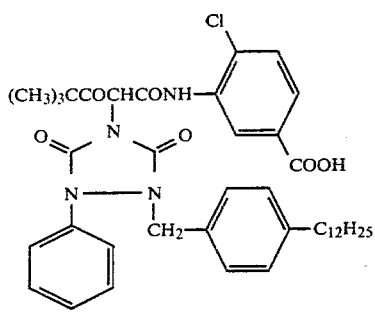
[VII-3] 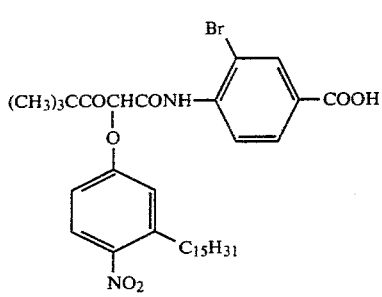
[VII-4] 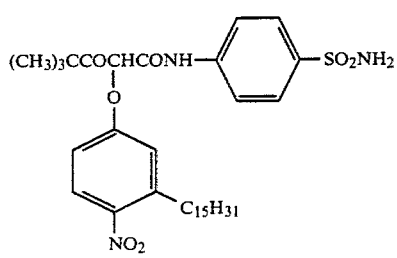
[VII-5] 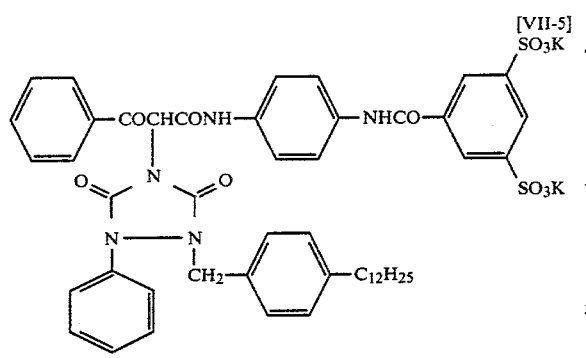
[VII-6] 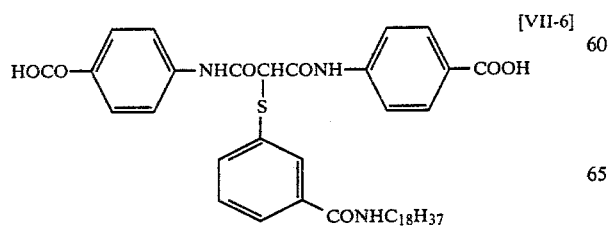
-continued
(Example compounds)
[VII-7]  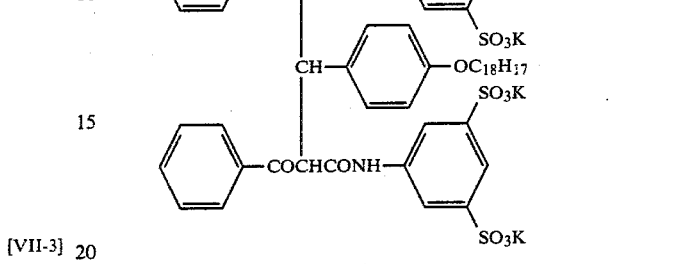
[VII-8] 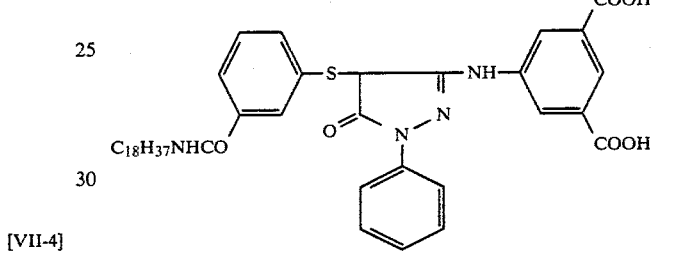
[VII-9] 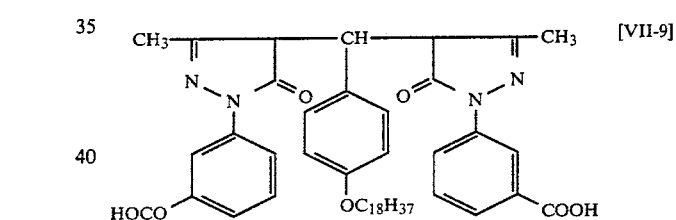
[VII-10] 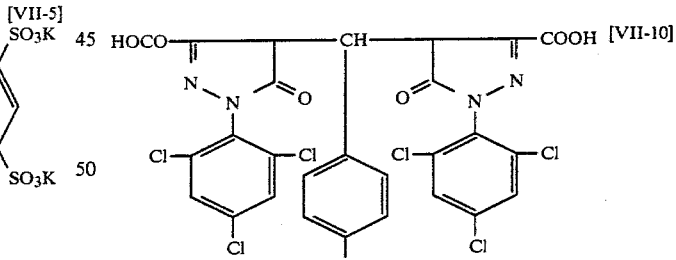
[VII-11] 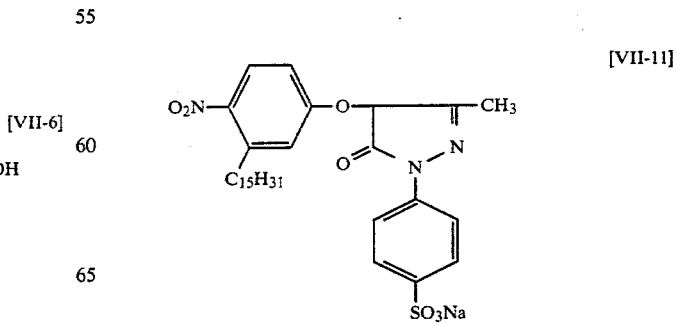

-continued
(Example compounds)
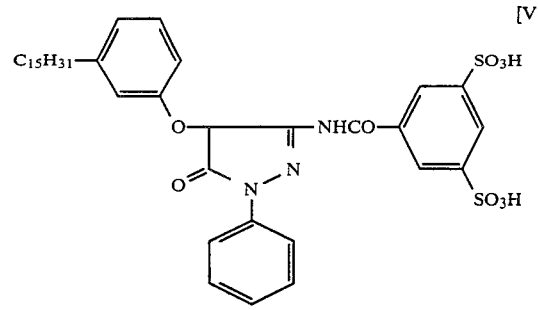 [VII-12]
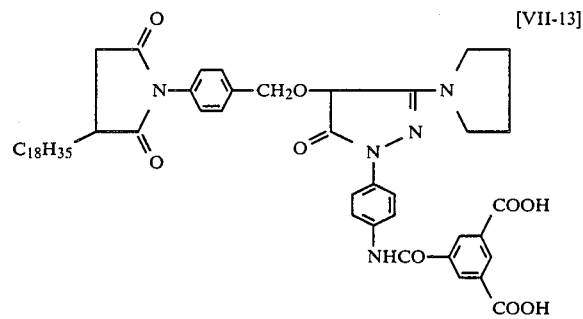 [VII-13]
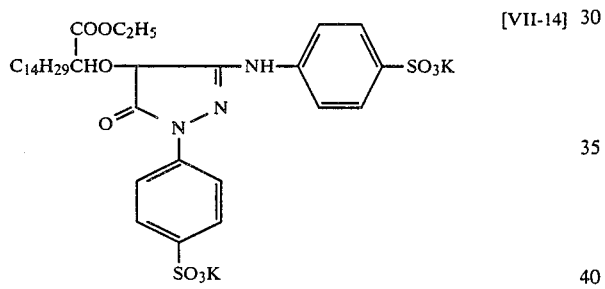 [VII-14]
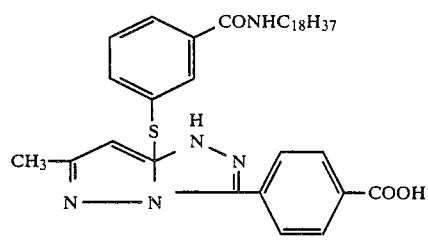 [VII-15]
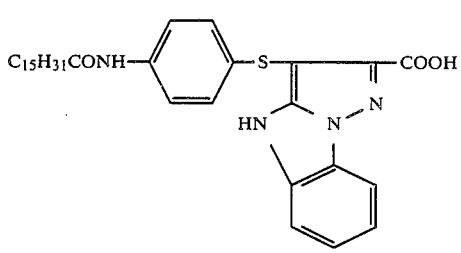 [VII-16]
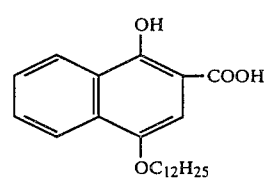 [VII-17]
-continued
(Example compounds)
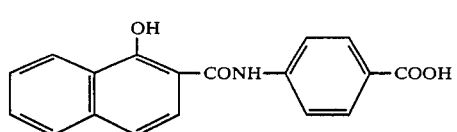 [VII-18]
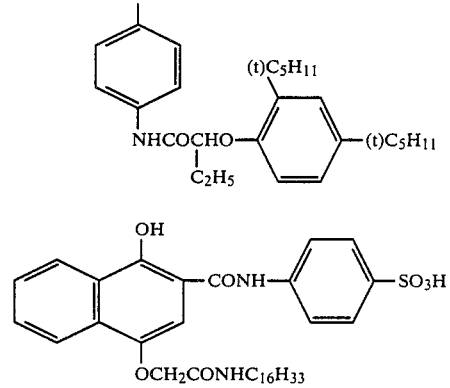 
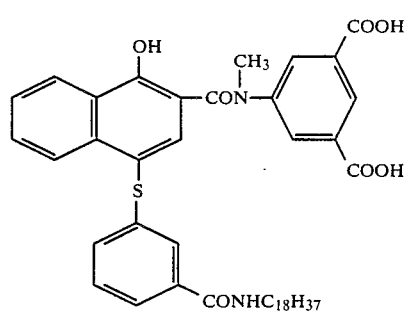 [VII-19]
[VII-20]
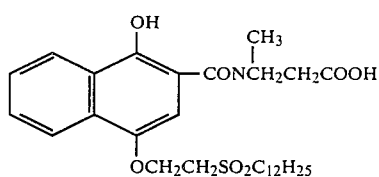 [VII-21]
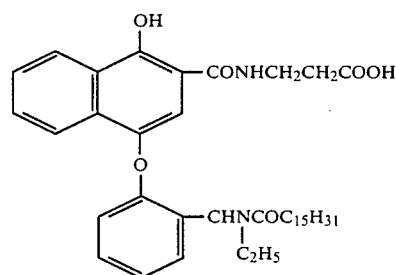 [VII-22]
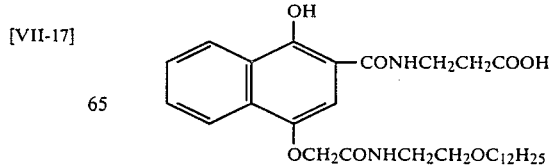 [VII-23]

-continued
(Example compounds)

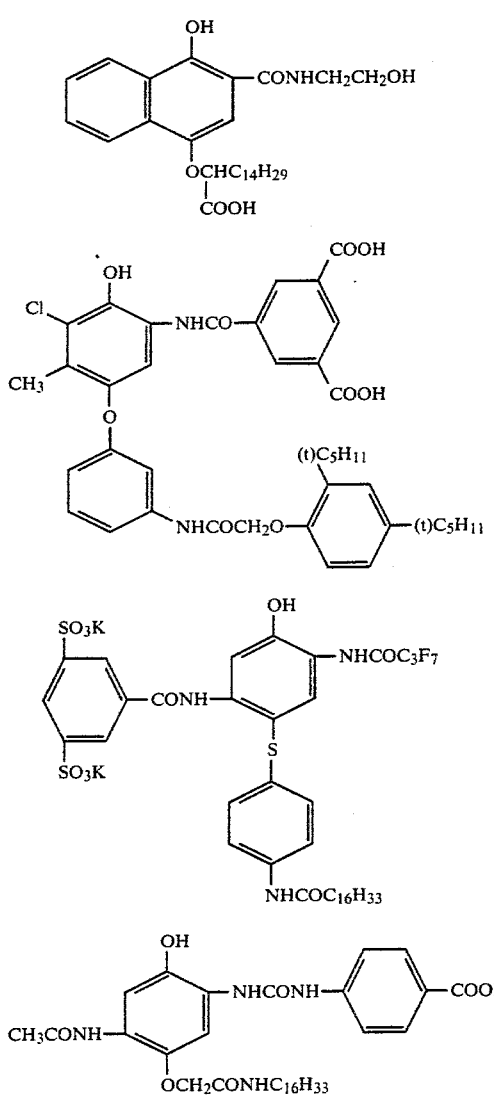

Having thus enumerated specific examples of the compounds of this invention, the compounds, including both of those as enumerated above and other compounds of this invention, may be used either singly or as a combination of two or more kinds.

In the following, representative synthesis examples about these compounds according to this invention are described, but other compounds can also easily be synthisized according to the procedures similar to these synthetic methods.

SYNTHESIS EXAMPLE 3

(Synthesis of example compound 80VII - 2])

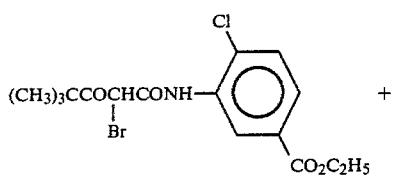

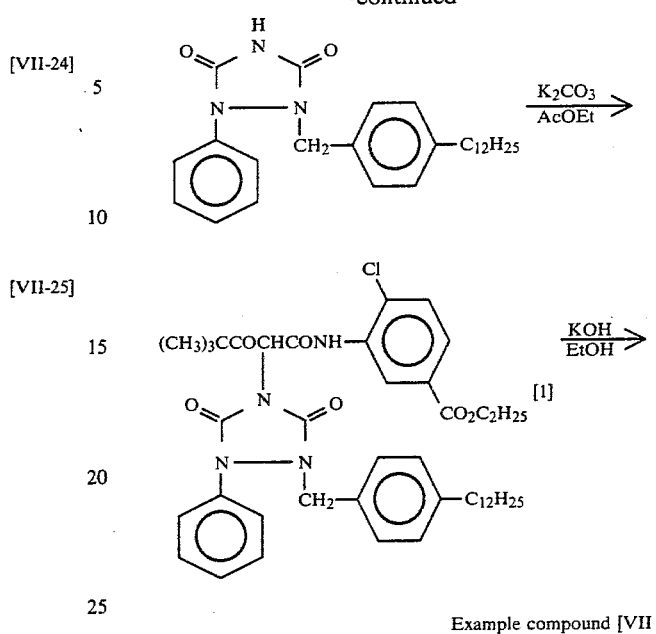

Example compound [VII - 2]

(a) Synthesis of the above [1]

To a solution of 7.4 g (0.018 mol) of α-pivalyl-α-bromo-2-chloro-5-ethoxycarbonylacetanilide and 8.0 g (0.018 mol) of 3-phenyl-4-(4-dodecylbenzyl)urazole in 100 ml of of ethyl acetate, 1.3 g (0.009 mol) of anhydrous potassium carbonate was added, and the mixture was refluxed for 3 hours. The reaction product was mixed with 200 ml of water for extraction of the ethyl acetate layer, followed by concentration, to give the above [1] as a yellow viscous material.

(b) Synthesis of example compound [VII - 2]

The compound [1] obtained in (a) was dissolved in 50 ml of ethyl alcohol, a solution of 5.0 g of potassium hydroxide dissolved in 10 ml of water was added thereto and the reaction was carried out for 2 hours. When the reaction product was added into ice-water containing 10 ml of conc. hydrochloric acid under stirring, white solid was precipitated. This was filtered, washed with water and dried, followed by recrystallization from ethyl acetate-n-hexane, to give 10.3 g of the example compound [VII - 2].

Mass spectrum: m/e=731 (M$^+$+1)

SYNTHESIS EXAMPLE 4

(Synthesis of example compound [VII - 9])

To a solution of 10.6 g (0.024 mol) of 1-(3-carboxyphenyl)-3-methylpyrazolone and 9.1 g (0.012 mol) of 4-octadecyloxy benzaldehyde dissolved in 200 ml of ethyl alcohol, 3 drops of triethylamine were added and the reaction was carried out for 5 hours. The solid obtained after concentration was washed with ethyl acetate to give 14.6 g of the example compound [VII - 9].

Mass spectrum: m/e=792 (M$^+$).

SYNTHESIS EXAMPLE 5

(Synthesis of example compound [VII - 18])

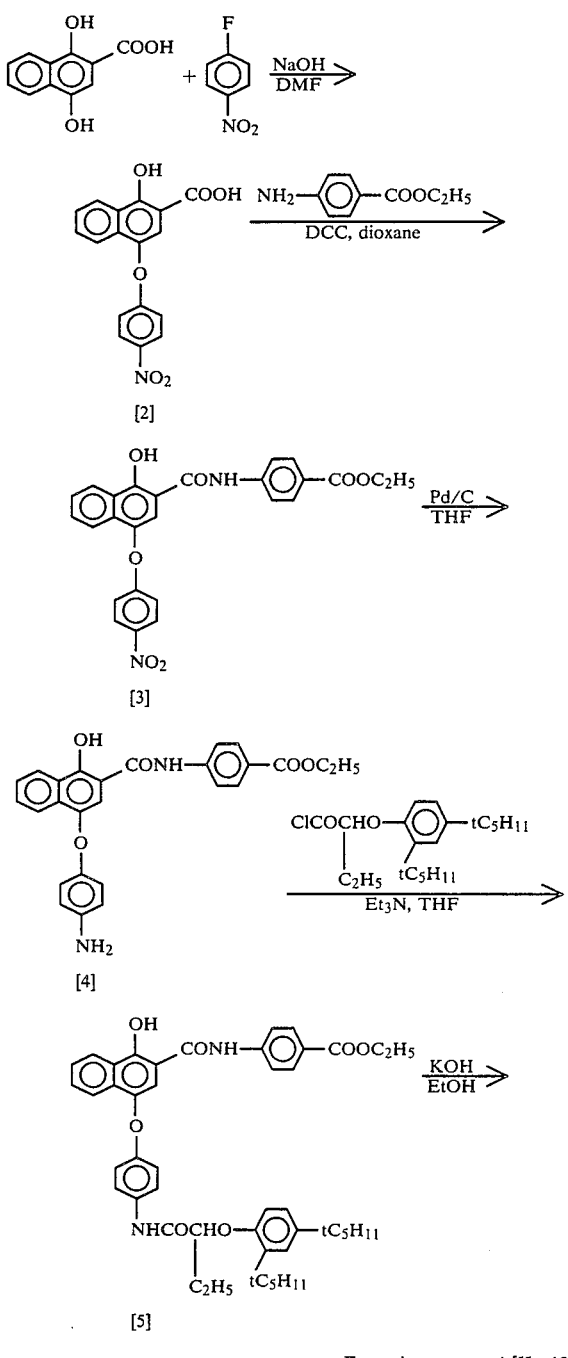

Example compound [II - 18]

(a) Synthesis of the above [2]

While nitrogen gas was bubbled into a solution of 20.4 g (0.1 mol) of 1,4-dihydroxy-2-naphthoic acid and 14.1 g (0.1 mol) of p-nitrofluorobenzene dissolved in 300 ml of dimethylformamide, a solution of 8.5 g of sodium hydroxide in 20 ml of water was added thereto, and the reaction was carried out for one hour. When the reaction product was added into ice-water containing 20 ml of hydrochloric acid, it was formed into a viscous mass. When this mass was stirred by heating on a water bath, it was then solidified. The crystals obtained were filtered, washed with water, washed with acetonitrile and dried to obtain 23.2 g of [2] as pale yellow solid.

(b) Synthesis of the above [3]

To a solution of 21.8 g (0.067 mol) of [2] obtained in (a) and 11.1 g (0.067 mol) of ethyl p-aminobenzoate dissolved in 200 ml of dioxane, 13.8 g (0.067 mol) of N,N'-dicyclohexylcarbodiimide was added and the reaction was carried out. The precipitated urea was separated by filtration, and the urea was further washed three times with 20 ml of hot dioxane. The filtrate was concentrated, and the resultant solid was washed with hot ethyl acetate to give 21 g of [3] as a yellowish green solid.

(c) Synthesis of the above [4]

The compound [3] obtained in (b) (21 g) was dissolved in 450 ml of tetrahydrofuran and catalytic hydrogenation was conducted for 10 hours with the use of 4 g of a 5% palladium/carbon catalyst. After removal of the catalyst, the solid obtained after concentration was washed with ethyl alcohol to obtain 9.2 g of [4] as a white solid.

(d) Synthesis of the above [5]

To a solution of 9.2 g (0.021 mol) of [4] obtained in (c) and 7.1 g (0.021 mol) of α-(2,4-di-t-pentylphenoxy)-butyroyl chloride dissolved in 100 ml of tetrahydrofuran, 1.7 g (0.021 mol) of pyridine was dissolved and the reaction was carried out for 2 hours. The pyridinium hydrochloride was filtered and concentrated to obtain a reddish brown viscous material. Silica gel column treatment with a solvent mixture of chloroform-n-hexane 1:1 gave 10 g of [5] as a pale yellow viscous material.

(e) Synthesis of example compound [VII - 18]

The compound [5] (7 g) obtained in (d) was dissolved in 50 ml of ethyl alcohol and a solution of 6.0 g of potassium hydroxide dissolved in 10 ml of water was added to the resultant solution, followed by the reaction for 3 hours. When the reaction product was added into ice-water containing 10 ml of conc. hydrochloric acid under stirring, white crystals were formed. The crystals were filtered, washed with water and then with acetonitrile. Recrystallization from acetonitrile-ethyl acetate gave 4.7 g of the example compound [VII - 18].

Mass spectrum: m/e=717 ($M^+ +1$)

The compound according to this invention contained in the intermediate layer may be added in an amount, which is not particularly limited, but preferably up to $8 \times 10^{-2}$ mole/m$^2$, more preferably up to $3 \times 10^{-2}$ mole/m$^2$, the lower limit being approximately $1 \times 10^{-7}$ mole/m$^2$.

The intermediate layer according to this invention can also incorporate, in addition to the compound according to this invention, other kinds of diffusion resistant couplers for photography, hydroquinone derivatives for controlling progress of development, couplers exhibiting no color, fine grains of silver halide and others. Said intermediate layer may also be constituted of two or more layers.

In general, light-sensitive materials containing couplers are constituted of a red-sensitive silver halide emulsion layer containing a diffusion resistant coupler for photography for cyan color formation, a green-sensitive emulsion layer containing a coupler for magenta color formation and a blue-sensitive emulsion layer containing a coupler for yellow color formation. The wording "substantially the same in color sensitiveness"

as used in this specification means having the sensitive region in substantially the same spectral region, indicating broadly demarcation between the three color regions of red, green and blue, and the sensitive regions with slight changes in spectrum are to be regarded as substantially the same. Also, when the light-sensitive material is applied for each layer of red-sensitive, green-sensitive and blue-sensitive layers, marked effects can be recognized, respectively. But, such a constitution is not imperative and a preferable result can be obtained when at least the green-sensitive layer takes the embodiment of the present invention. Thus, application of the present invention for all of the color-sensitive layers should be appreciated as an embodiment for creating further excellent image quality of the final color image.

In the intermediate layer according to this invention, two or more kinds of the compounds according to this invention may be employed in combination. When two or more kinds of compounds are employed, at least one of the compounds according to this invention to be contained in the intermediate layer according to this invention should preferably have a coupling speed which is equal to or greater than the greatest coupling speed among the diffusion resistant couplers for photography contained in the high sensitivity emulsion layer. The compound according to this invention, having a coupling speed which is equal to or greater than the greatest coupling speed among the diffusion resistant couplers for photography contained in the high sensitivity emulsion layer, should preferably be contained at a proportion of 30% or more, particularly preferably 70% or more, of the above compounds according to this invention and/or various compounds as mentioned above.

Comparison of the coupling speed of the aforesaid couplers or compounds contained in the high sensitivity emulsion and the intermediate layer according to this invention is conducted by adding 0.02 mole of each coupler or 0.05 mole of each compound per mole of silver halide into a silver halide emulsion prepared according to the method well known in the art, performing sensitometry generally known in the art and comaring the sensitivities at the fog density of +0.1. During this operation, comparison is made with the amount of silver developed between the respective samples under the same exposure conditions after being subjected to the treatment process of the fixing step et seq without carrying out bleaching step after color developing. As for the coupling speed, the coupler or the compound according to this invention used in the sample in which the amount of silver develop is greater formed is defined as being more rapid in coupling speed. Couplers or compounds of the present invention are added according to the method, in which 0.02 mole of a coupler is dissolved by heating in a mixed solvent of 0.04 mole of tricresyl phosphate and 0.5 mole of ethyl acetate, thereafter mixing the resultant solution with an aqueous gelatin solution containing sodium dodecylbenzene sulfonate and then emulsifying the mixture by means of a high speed rotary mixer, followed by addition into the silver halide emulsion. The coupler insoluble in the above mixed solvent is dissolved together with a high boiling solvent at equal moles in a solvent capable of dissolving the coupler, emulsified and added.

As preferable ones among the compounds according to this invention, there may significantly be used those which can give greater amounts of the developed silver in the above comparison method for coupling speed.

According to this invention, the light-sensitive material of this invention can contain, in the light-sensitive layer comprising a plural number of silver halide emulsion layers having substantially the same color sensitiveness and different sensitivities, diffusion resistant couplers for photography capable of forming diffusion resistant color forming dyes to give color tones corresponding to said sensitiveness. For example, the diffusion resistant cyan couplers for photography as mentioned above may preferably be phenol type compounds or naphthol type compounds, which may be selected from those disclosed in, for example, U.S. Pat. Nos. 2,369,929; 2,434,272; 2,474,293; 2,895,826; 3,253,924; 3,034,892; 3,311,476; 3,386,301; 3,419,390; 3,458,315; 3,476,563 and 3,591,383, and the methods for synthesis thereof are also disclosed in these specifications.

The diffusion resistant magenta couplers for photography to be used in the present invention may include compounds of the pyrazolone type, the pyrazolotriazole type, pyrazolinobenzimidazole type and the indazolone type. As the pyrazolone type magenta couplers, there may be included the compounds disclosed in U.S. Pat. Nos. 2,600,788; 3,062,653; 3,127,269; 3,311,476; 3,419,391; 3,519,429; 3,558,318; 3,684,514 and 3,888,680; and Japanese Provisional Patent Publications Nos. 29639/1974, 11163/1974, 29538/1974 and 13041/1975. As the pyrazolotriazole type magenta couplers, there are the compounds as disclosed in U.S. Pat. No. 1,247,493 and Belgian Patent No. 792,525. The pyrazolinobenzimidazole type magenta couplers may be, for instance, those disclosed in U.S. Pat. No. 3,061,432; West German Pat. No. 2,156,111; and Japanese Patent Publication No. 60479/1971. Further, the indazolone type magenta couplers may include the compounds disclosed in Belgian Pat. No. 769,116. All of these compounds can be advantageously used in the present invention.

As the diffusion resistant yellow couplers for photography to be used in this invention, open-chain ketomethylene compounds have been used, and there may be included the benzoylacetanilide type yellow couplers and the pivaloylacetanilide type yellow couplers, which have generally widely been used. Further, the divalent type yellow couplers, in which the carbon atom at the coupling position is substituted with a substituent which can be eliminated during coupling reaction, may also advantageously be used. Examples of these compounds are disclosed, together with their synthetic methods, in U.S. Pat. Nos. 2,875,057; 3,265,506; 3,664,841; 3,408,194; 3,447,928; 3,277,155 and 3,415,652; Japanese Patent Publication No. 13576/1974; and Japanese Provisional Patent Publications Nos. 29432/1973, 66834/1973, 10726/1974, 122335/1974, 28834/1975 and 132926/1975.

In this invention, it is also possible to employ a colored coupler in combination with the diffusion resistant coupler for photogaphy as described above, if desired. For example, as the diffusion resistant colored cyan coupler for photography to be used, there may generally be used phenol or naphthol derivatives, as exemplified by those disclosed, together with their synthetic methods, in U.S. Pat. Nos. 2,521,908 and 3,034,892; U.K. Pat. No. 1,255,111; Japanese Provisional Patent Publications Nos. 22028/1973, 123341/1975 and No. 10135/1975; and U.S. Pat. No. 3,476,563. As the diffusion resistant colored magenta coupler for photography to be used in the present invention, there may generally be used compounds arylazo-substituted at the coupling position of colorless magenta couplers, such as those disclosed in U.S. Pat. Nos. 2,801,171; 2,983,608; 3,005,712 and 3,684,514; U.K. Pat. No. 937,621; and Japanese Provisional Patent Publications Nos. 123625/1974 and 31448/1974. Further, it is also possible to use a colored magenta coupler of the type in which the dye is flown out into the treating solution through reaction with the oxidized product of a developing agent, as disclosed in U.S. Pat. No. 3,419,391.

The amount of the above diffusion resistant coupler for photography in this invention may generally range from $2 \times 10^{-3}$ mole to $5 \times 10^{31}$ $^1$ mole per mole of silver in the light-sensitive silver halide emulsion layer, preferably from $5 \times 10^{-3}$ mole to $5 \times 10^{-2}$ mole in the high sensitivity emulsion layer, and from $2 \times 10^{-2}$ mole to $3 \times 10^{-1}$ mole in the low sensitivity emulsion layer. In the intermediate layer according to this invention, it may be added in an amount which does not impair the effect of the compound of this invention, namely from $1 \times 10^{-7}$ mole/dm$^2$ to $8 \times 10^{-3}$ mole/dm$^2$, preferably from $4 \times 10^{-6}$ mole/dm$^2$ to $3 \times 10^{-3}$ mole/dm$^2$.

The compound according to this invention and other kinds of diffusion resistant couplers for photography to be used in this invention may be dispersed according to various methods such as the so-called alkaline aqueous dispersing method, the solid dispersing method and the oil droplet-in-water type dispersing method, which may suitably be selected depending on the chemical structure or others of the diffusion resistant coupler employed.

In this invention, the latex dispersing method or the oil droplet-in-water type emulsion dispersing method is particularly effective. These dispersing methods are well known in the art, and the latex dispersing method and its effect are described in Japanese Provisional Patent Publications Nos. 74538/1974, 59943/1976 and 32552/1979; and Research Disclosure No. 14850, pp. 77–79, August 1976.

Suitable latices may include homopolymers, copolymers and terpolymers of monomers such as styrene, ethyl acrylate, n-butyl acrlate, n-butyl methacrylate, 2-acetoacetoxyethyl methacrylate, 2-(methacryloyloxy)ethyltrimethylammonium methosulfate, sodium 3-(methacryloyloxy)propane-1-sulfonate, N-isopropylacrylamide, N-[2-(2-methyl-4-oxopentyl)]acrylamide, 2-acrylamido-2-methylpropane sulfonic acid, etc. In the oil droplet-in-water type emulsion dispersing method, there may be employed a method known in the art for dispersing a hydrophobic additive such as couplers. For example, after dissolving in a single kind or a solvent mixture selected from high boiling point organic solvents having boiling points of 175° C. or higher such as tricresyl phosphate, dibutyl phthalate and/or low boiling point organic solvents such as ethyl acetate, butyl propionate, etc., the resultant mixture is dissolved in an aqueous solution containing a surfactant, followed by emulsification by means of a high speed rotatary mixer or a colloid mill, and the resultant emulsion is added directly into a silver halide emulsion layer or an intermediate layer, or alternatively said emulsion after stripping the low boiling solvent therefrom according to a known method may be added into the silver halide emulsion or the intermediate layer according to this invention.

Further, the colorless couplers to be used in combination with this invention may be selected from those disclosed in U.K. Pat. Nos. 861,138, 914,145 and 1,109,963; Japanese Patent Publication No. 14033/1970; U.S. Pat. No. 3,580,722; and Mitteilungen aus den Forschunings Laboratorien der Agfa Leberkusen Vol. 4, pp. 352–367, 1964.

Also, for enhancing the effect of this invention, it is preferred to incorporate a compound capable of releasing a development inhibitor through the reaction with the oxidized product of a developing agent (hereinafter called as DIR compound) in the high sensitivity emulsion layer, the low sensitivity emulsion layer and/or the intermediate layer therebetween according to the embodiments as described above. DIR compounds are described in detail in, for example, U.S. Pat. No. 3,227,554 or Japanese Provisional Patent Publication No. 45315/1979. A DIR compound may be used in the above-mentioned constituent layers in an amount up to 2 mg/dm$^2$, particularly preferably from 0.1 up to 0.9 mg/dm$^2$.

Further, other than the embodiments as described above, this invention can be preferably be applied for a light-sensitive material having at least one light-sensitive layer, which has 3 or more silver halide emulsion layers with different sensitivities. For example, preferable effect of this invention can be also exhibited by an embodiment in which the above-mentioned light-sensitive layer has a constitution comprising a silver halide emulsion layer with the highest sensitivity on the side farthest from the support side, an intermediate layer according to this invention and two or more silver halide emulsion layers with sequentially lowered sensitivities provided successively on the support.

As the silver halide to be used in the silver halide emulsion, there may be included any one conventionally used in silver halide photographic emulsions such as silver chloride, silver bromide, silver iodide, silver chlorobromide, silver iodobromide, silver chloroiodobromide and mixtures thereof.

The silver halide grains may be either coarse or fine, and the distribution of the grain sizes may be either narrow or broad. The crystals of these silver halide grains may be either normal or twin crystals, and the crystals with any desired ratio of [100] plane to [111] plane may be available. These silver halide grains may have a crystalline structure which is uniform from the inner portion to the outer portion, or a layered structure with different inner and outer layers. Further, these silver halides may be either of the type forming latent images on its surface or of the type forming latent images internally of the grains. These silver halide grains can be prepared according to any of the methods known in the art.

The silver halide emulsion to be used in this invention may preferably be one from which soluble salts have been removed, but it is also possible to use one without removal of such salts. Also, two or more kinds of silver halide emulsions prepared separately can be used as a mixture.

As the binder for the silver halide emulsion layer in the light-sensitive material of this invention, there may be used those known in the art, for example, most preferably gelatin or otherwise gelatin derivatives such as phenylcarbamylated gelatin, acylated gelatin phthalated gelatin, etc., which may be also be added as a compatible mixture, if desired.

The silver halide emulsion having the above-described silver halide grains in a binder solution can be sensitized with a chemical sensitizer. Chemical sensitizers to be used advantageously in this invention may be classified broadly into the four kinds of noble metal sensitizers, sulfur sensitizers, selenium sensitizers and reducing sensitizers, and these may also be used in combination.

Noble metal sensitizers may include gold compounds and compounds of ruthenium, rhodium, palladium, iridium and platinum.

When a gold compound is used, ammonium thiocyanate or sodium thiocyanate may be used in combination.

Sulfur sensitizers may include, in addition to active gelatin, sulfur compounds.

Selenium sensitizers may include active and inactive selenium compounds.

As the reducing sensitizers, there are monovalent tin salts, polyamine, bisalkylaminosulfide, silane compounds, iminoaminomethanesulfinic acid, hydrazinium salts, hydrazine derivatives, etc.

In the light-sensitive material of this invention, in addition to the additives as described above, it is also possible to use various additives useful for light-sensitive material such as stabilizers, development accelerators, film hardeners, surfactants, contamination preventives, lubricants, UV-ray absorbers, etc.

The light-sensitive material of this invention can also conveniently have any auxiliary layer, e.g. protective layer, other intermediate layers, filter layer, halation preventive layer, back layer, etc. in addition to the silver halide emulsion layer and the intermediate layer according to this invention.

The support to be used in the light-sensitive material of this invention may be suitably selected from those known in the art depending on the purpose of use of the light-sensitive material, such as plastic films, plastic laminated papers, baryta papers, synthetic papers, etc. These supports are generally applied with subbing treatment for reinforcement of adhesion to the photographic emulsion layer.

Now, preferable embodiments of the primary constituting layers in the color light-sensitive material according to this invention are set forth below. The layers are arranged in the order from the surface layer side toward the support side.

EXAMPLE CONSTITUTION 1

1. Blue-sensitive silver halide emulsion layer containing one layer or two or more layers of diffusion resistant yellow couplers for photography;
2. Yellow filter layer which can absorb blue light;
3. High sensitivity green-sensitive emulsion layer containing a diffusion resistant magenta coupler for photography;
4. Intermediate layer containing a diffusion resistant coupler or a compound according to this invention;
5. Low sensitivity green-sensitive emulsion layer containing a diffusion resistant magenta coupler for photography;
6. Red-sensitive silver halide emulsion layer containing one layer or two or more layers of diffusion resistant cyan couplers for photography;
7. Support.

EXAMPLE CONSTITUTION 2

1. Blue-sensitive silver halide emulsion layer containing one layer or two or more layers of diffusion resistant yellow couplers for photography;
2. Yellow filter layer which can absorb blue light;
3. High sensitivity green-sensitive emulsion layer containing a diffusion resistant magenta coupler for photography;
4. Intermediate layer containing a diffusion resistant coupler or a compound according to this invention;
5. Low sensitivity green-sensitive emulsion layer containing a diffusion resistant magenta coupler for photography at a density lower relative to the layer 6 below;
6. Low sensitivity green-sensitive emulsion layer containing a diffusion resistant magenta coupler for photography at a density higher relative to the layer 5 above;
7. Red-sensitive silver halide emulsion layer containing one layer or two or more layers of diffusion resistant cyan couplers for photography;
8. Support.

EXAMPLE CONSTITUTION 3

1. Blue-sensitive silver halide emulsion layer containing one layer or two or more layers of diffusion resistant yellow couplers for photography;
2. Yellow filter layer which can absorb blue light;
3. High sensitivity green-sensitive emulsion layer containing a diffusion resistant magenta coupler for photography;
4. High sensitivity red-sensitive emulsion layer containing a diffusion resistant cyan coupler for photography;
5. Intermediate layer containing a diffusion resistant coupler or a compound according to this invention;
6. Low sensitivity red-sensitive emulsion layer containing a diffusion resistant magenta coupler for photography;
7. Support.

The color light-sensitive material of this invention as described above can be exposed to light and thereafter subjected to a color developing method conventionally employed to obtain images. The basic processing steps include color developing, bleaching and fixing steps. These respective basic processing steps may be sometimes performed independently, or alternatively in place of performing 2 or more processing steps, one processing may be performed with a processing liquor having those functions. For example, there may be employed one-bath color processing method wherein the bath contains a color developing agent, a ferric salt bleaching component and a thiosulfate fixing component or one-bath bleach-fixing method wherein the bath contains a bleaching component of ethylendiamine tetraacetic iron (III) complex salt and a thiosulfate fixing component.

For the light-sensitive material, all of the treating methods may be applicable. Typical examples may include the method, in which after color developing, bleach-fixing processing is performed, followed further by washing with water, stabilizing processing, if desired; the method, in which pre-film-hardening, neutralization, color developing, stopping fixing, washing with water, bleaching, fixing, washing with water, post-film-hardening and washing with water are performed in the order mentioned; the method in which color developing, washing with water, supplementary color developing, stopping, bleaching, fixing, washing with water and stabilizing are performed in the order mentioned; the developing method in which the developed silver after halogenation bleach is subjected again to color developing to increase the amount of dye formed; the method for treating a low silver content light-sensitive material with the use of an amplifier agent such as a peroxide or a cobalt salt; and others.

The color developing agent may be selected typically from those of the p-phenylenediamine type.

The precursor for a color developing agent to be used in the present invention, which can be used by addition in the light-sensitive color photographic material may include Schiff base type for color developers as disclosed in U.S. Pat. Nos. 2,507,114; 2,695,234 and 3,342,599 or Research Disclosure Vol. 151, No. 15159, November 1979 and also those as disclosed in Research Disclosure Vol. 129, No. 12924, October 1976; ibid Vol. 121, No. 12146, June 1974; and ibid Vol. 139, No. 13924, November 1975.

Various additives may also be added into the color developing liquor, if desired.

The present invention is further illustrated by referring to the following Examples, by which the present invention is not limited.

EXAMPLE 1

Each of Samples 1, 2, 3, 4, 5 and 6 was prepared by providing by way of coating the respective layers as shown below successively on a support of a cellulose triacetate film applied with subbing treatment.

SAMPLE—1

Layer 1: Low sensitivity green-sensitive silver halide emulsion layer

A silver iodobromide containing 6 mole % of silver iodide (average grain size $0.5\mu$, containing 0.25 mole of silver halide and 40 g of gelatin per 1 kg of emulsion) was prepared in a conventional manner and 1 kg of this emulsion was chemically sensitized with gold and sulfur sensitizers, and further mixed with, as green sensitive sensitizing dyes, 32.5 mg of anhydrous 5,5'-dichloro-9-ethyl-3,3'-di-(3-sulfopropyl)oxacarbocyanine hydroxide; 55 mg of anhydrous 5,5'-diphenyl-9-ethyl-3,3'-di-(3-sulfopropyl)oxacarbocyanine hydroxide; and 42.5 mg of anhydrous 9-ethyl-3,3'-di-(3-sulfopropyl)-5,6,5',6'-dibenzoxacarbocyanine hydroxide, followed by addition of 0.25 g of 4-hydroxy-6-methyl-1,3,3a,7-tetrazaindene, 20 mg of 1-phenyl-5-mercaptotetrazole, 0.5 g of polyvinyl pyrrolidone and 500 ml of the dispersion (M-1) shown below to prepare a low sensitivity green sensitive silver halide emulsion, which was then applied to a dry film thickness of $3.0\mu$.

Layer - 2...Intermediate layer

An aqueous gelatin solution was applied to a dry film thickness of $1.0\mu$.

Layer - 3...High sensitivity green-sensitive silver halide emulsion layer

A silver iodobromide containing 7 mole % of silver iodide (average grain size 0.9 $\mu$, containing 0.25 mole of silver halide and 30 g of gelatin per 1 kg of emulsion) was prepared in a conventional manner and 1 kg of this emulsion was chemically sensitized with gold and sulfur sensitizers, and further mixed with, as green sensitive sensitizing dyes, anhydrous 5,5'-dichloro-9-ethyl-3,3'-di-(3-sulfopropyl)oxacarbocyanine hydroxide; anhydrous 5,5'-diphenyl-9-ethyl-3,3'-di-(3-sulfopropyl)oxacarbocyanine hydroxide; and anhydrous 9-ethyl-3,3'-di-(3-sulfopropyl)-5,6,5',6'-dibenzoxacarbocyanine hydroxide, followed by addition of 0.25 g of 4-hydroxy-6-methyl1,3,3a,7-tetrazaindene, 5 mg of 1-phenyl-5-mercaptotetrazole, 0.2 g of polyvinyl pyrrolidone and 200 ml of the dispersion (M-2) shown below to prepare a high sensitivity green sensitive silver halide emulsion, which was then applied to a dry film thickness of $2.0\mu$.

Layer - 4...Yellow filter layer

An aqueous gelatin solution having yellow colloidal silver dispersed therein was applied to dry film thickness of $1.2\mu$, with the gelatin being at a proportion of 0.9 g/m$^2$ and a silver of 0.12 g/m$^2$.

Sample - 2

Sample - 2 was prepared in the same manner as in preparation of Sample - 1, except that the intermediate layer of Layer - 2 in Sample - 1 was replaced with the intermediate layer which was prepared by adding the dispersion (AS) shown below in the aqueous gelatin solution employed for Layer - 2 in Sample - 1 and applying the mixture to a dry film thickness of 1.0 $\mu$, with 2,5-di-t-octyl- hydroquinone content of 0.07 g/m$^2$.

Sample - 3

Sample - 3 was prepared similarly as Sample - 2 except for the dispersion (M - 3) shown below in place of the dispersion (AS) employed for the Layer - 2 in Sample 2.

Sample - 4

Sample - 4 was prepared similarly as Sample - 2 except for the dispersion (M - 4) shown below in place of the dispersion (AS) employed for the Layer - 2 in Sample 2.

Sample - 5

Sample - 5 was prepared similarly as Sample - 2 except for the dispersion (M - 5) shown below in place of the dispersion (AS) employed for the Layer - 2 in Sample 2.

Sample - 6

Layer - 1...Low sensitivity green-sensitive silver halide emulsion layer

The same layer as Layer - 1 in Sample 1

Layer - 2...Intermediate layer

The same layer as Layer - 2 in Sample 1 except for the dry film thickness which is $0.5\mu$ Layer - 3...Intermediate layer The same layer as Layer - 2 in Sample - 5

Layer - 4...Intermediate layer

The same layer as Layer - 2 in Sample - 6

Layer - 5...High sensitivity green-sensitive silver halide emulsion layer

The same layer as Layer - 3 in Sample 1

Layer - 6...Yellow filter layer

The same layer as Layer - 4 in Sample 1

The dispersions employed in the above respective emulsion layers were prepared as follows:

Dispersion (M - 1)

A solution of 54 g of the magenta coupler (M - 1) shown below, 14 g of the colored magenta coupler (CM - 1), 0.5 g of the DIR compound (D - 3) and 0.5 g of the DIR compound (D - 1) as shown below dissolved in a mixture of 68 g of tricresyl phosphate (TCP) and 280 ml of ethyl alcohol (EA) was added to 500 ml of a 7.5% gelatin solution containing 8 g of sodium triiropropylnaphthalene sulfonate, followed by emulsification in a colloid mill, to be made up to 1,000 ml.

Dispersion (M - 2)

A solution of 30 g each of the magenta couplers (M - 1) and (M - 2) shown below, 12 g of the colored magenta coupler (CM - 1) and 0.3 g of the DIR compound (D - 2) shown below dissolved in a mixture of 70 g of TCP and 280 ml of EA was added into 500 ml of a 7.5% gelatin solution containing 8 g of sodium triisopropylnaphthalene sulfonate, followed by emulsification in a colloid mill, to be made up to 1,000 ml.

Dispersion (AS)

A solution of 50 g of 2,5-di-tert-octylhydroquinone dissolved in a mixture of 50 g of TCP and 100 ml of EA was added into 500 ml of a 7.5% aqueous gelatin solution containing 6 g of sodium triisopropylnaphthalene sulfonate, followed by emulsification in a colloid mill, to be made up to 800 ml.

Dispersion (M - 3)

A solution of 60 of the magenta coupler (M - 3) shown below dissolved in a mixture of 60 g of TCP and 180 ml of EA was added into 500 ml of a 7.5% gelatin solution containing 8 g of sodium triisopropylnaphthalene sulfonate, followed by emulsification in a colloid mill, to be made up to 1,000 ml.

Dispersion (M - 4)

Prepared by dispersing in the same manner as in preparation of Dispersion (M - 3) except that the Example compound [I - 5] of this invention was employed as the magenta coupler in place of the magenta coupler (M - 3).

Dispersion (M - 5)

Prepared by dispersing in the same manner as in preparation of Dispersion (M - 3) except that the Example compound [I - 4] of this invention was employed as the magenta coupler in place of the magenta coupler (M - 3).

Magenta coupler (M - 1):
1-(2,4,6-trichlorophenyl)-3-[3-(2,4-di-t-amylphenoxyacetamide)benzamido]-5-pyrazolone Magenta coupler (M - 2):
4,4'-methylenebis{1-(2,4,6-trichlorophenyl)-3-[3-(2,4-di-t-amylphenoxyacetamide)benzamido]-5-pyrazolone}

Magenta coupler (M - 3):
1-(2,4,6-trichlorophenyl)-3-[3-(2,4-di-t-amylphenoxyhexylamide)benzamido]-5-pyrazolone Colored magenta coupler (CM - 1):
1-(2,4,6-trichlorophenyl)-4-(1-naphthylazo)-3-(2-chloro-5-octadecenylsuccinimidoanilino)-5-pyrazolone DIR compound (D - 1):
2-(1-phenyl-5-tetrazolythio)-4-octadecylsuccinimido-1-indanone DIR compound (D - 2):
1-hydroxy-N-(2-n-tetradecyloxyphenyl)-4-[1-phenyl-3-methyl-4-(1-phenyl-5-tetrazolylthio)methyl-5-pyrazolyl-oxy]-2-naphthoamide DIR compound (D - 3):
2-(2-amino-1,3,4-thiadiazolyl-5-thio)-4-octadecylsuccinimido-1-indanone These samples were subjected to white light exposure through an optical wedge, followed by processing according to the following processing steps.

| Processing steps (38° C.) | Processing time |
|---|---|
| Color development | 2 minutes 10 seconds |
| Bleaching | 6 minutes 30 seconds |
| Washing with water | 3 minutes 15 seconds |
| Fixing | 6 minutes 30 seconds |
| Washing with water | 3 minutes 15 seconds |
| Stabilization | 1 minute 30 seconds |

The following processing solutions were used in the processing steps:

| [Composition of color developing solution] | |
|---|---|
| 4-Amino-3-methyl-N—ethyl-N—($\beta$-hydroxyethyl)aniline sulfate | 4.8 g |
| Anhydrous sodium sulfite | 0.14 g |
| Hydroxylamine ½ sulfate | 1.98 g |
| Sulfuric acid | 0.74 g |
| Anhydrous potassium carbonate | 28.85 g |
| Anhydrous potassium hydrogen carbonate | 3.46 g |
| Anhydrous potassium sulfite | 5.10 g |
| Potassium bromide | 1.16 g |
| Sodium chloride | 0.14 g |
| Trisodium nitrilotriacetate (monohydrate) | 1.20 g |
| Potassium hydroxide | 1.48 g |
| Made up to 1 liter with water. | |

| [Composition of bleaching solution] | |
|---|---|
| Ferric ammonium salt of ethylenediaminetetraacetic acid | 100.0 g |
| Diammonium salt of ethylenediaminetetraacetic acid | 10.0 g |
| Ammonium bromide | 150.0 g |
| Glacial acetic acid | 10.0 ml |
| Made up to 1 liter with water and adjusted to pH 6.0 with aqueous ammonia. | |

| [Composition of fixing solution] | |
|---|---|
| Ammonium thiosulfate | 175.0 g |
| Anhydrous sodium sulfite | 3.6 g |
| Sodium metasulfite | 2.3 g |
| Made up to 1 liter with water and adjusted to pH 6.0 with acetic acid. | |

| [Composition of stabilizing solution] | |
|---|---|
| Formalin (37% aqueous solution) | 1.5 ml |
| Konidax (available from Konishiroku Photo Industry Co., Ltd.) | 7.5 ml |
| Made up to 1 liter with water. | |

For each of the color image formed on each of the above Samples, the results of fog sensitivity and gamma on the same day and after storage for 3 days under the conditions of 55° C., 10% relative humidity, graininess and sharpness were measured. The results are shown in Table 1.

In the Tables, gamma and graininess are values measured when giving white light exposure and graininess (RMS) is shown in terms of 1000-fold values of the standard deviations of fluctuations in density values which occur during scanning by means of a microdensitometer with a circular scanning orifice diameter of 2.5μ.

Detection of image sharpness was conducted by determining MTF (Modulation Transfer Function) and making comparison between the greatness of MTF values at space frequencies of 10 lines/mm and 30 lines/mm.

were mixed at a ratio of 1:1. Then, 500 ml of the dispersion (M - 1) was added to 1 kg of the mixed dispersion to prepare a low sensitivity green-sensitive silver halide emulsion, which was then applied to a dry film thickness of 3.0μ.

TABLE 1

| Sample No. | On the same day | | | Storability | | | Graininess (RMS) | | Sharpness (MTF) | |
|---|---|---|---|---|---|---|---|---|---|---|
| | Fog | Sensitivity | Gamma | Fog | Sensitivity | Gamma | Fog + 0.1 | Fog + 0.4 | 10/mm | 30/mm |
| 1 (Comparative) | 0.13 | 100 | 0.57 | 0.13 | 100 | 0.56 | 32 | 45 | 90 | 37 |
| 2 (Comparative) | 0.13 | 98 | 0.58 | 0.16 | 85 | 0.65 | 29 | 40 | 95 | 45 |
| 3 (Comparative) | 0.14 | 100 | 0.59 | 0.14 | 100 | 0.58 | 33 | 50 | 92 | 42 |
| 4 (This invention) | 0.13 | 105 | 0.58 | 0.14 | 100 | 0.58 | 25 | 35 | 93 | 41 |
| 5 (This invention) | 0.12 | 100 | 0.58 | 0.13 | 100 | 0.59 | 23 | 30 | 93 | 40 |
| 6 (This invention) | 0.13 | 100 | 0.57 | 0.13 | 100 | 0.58 | 21 | 29 | 93 | 40 |

As apparently seen from the results in the above Table 1, excellent characteristics were exhibited in all of graininess, sharpness, storability and gradation in Samples 4 to 6 of this invention, as compared with Samples 1 to 3 for comparative purpose. In particular, in spite of addition of the mobile coupler of this invention in the intermediate layer, sharpness was not deteriorated but slightly improved. Such an effect is indeed surprising enough and cannot be expected within the scope of the prior art.

EXAMPLE 2

On a support of a cellulose triacetate layer applied with subbing treatment, the respective layers as shown below were provided by coating successively from the support side to prepare Samples 7, 8 and 9.

Sample - 7

Layer - 1...Low sensitivity green-sensitive silver halide emulsion layer

A silver iodobromide emulsion containing 6 mole % of silver iodide (average grain size 0.35 μ, containing 0.25 mole of silver halide and 40 g of gelatin per kg of emulsion) was prepared in a conventional manner and 1 kg of this emulsion was chemically sensitized with gold and sulfur sensitizers, and further mixed with, as green sensitive sensitizing dyes, anhydrous 5,5'-dichloro-9-ethyl-3,3'-di-(3-sulfopropyl)oxacarbocyanine hydroxide; anhydrous 5,5'-diphenyl-9-ethyl-3,3'-di-(3-sulfopropyl)-oxacarbocyanine hydroxide; and anhydrous 9-ethyl-3,3'-di-(3-sulfopropyl)-5,6,5', 6'-dibenzoxacarbocyanine hydroxide, followed by addition of 0.25 g of 4-hydroxy-6-methyl-1,3,3a,7-tetrazaindene, 20 mg of 1-phenyl-5-mercaptotetrazole, and 0.2 g of polyvinyl pyrrolidone to prepare a sensitized emulsion A. Also, a silver iodobromide emulsion containing 6 mole % of silver iodide (average grain size 0.35μ, containing 0.25 mole of silver halide and 40 g of gelatin per kg of emulsion) was prepared in a conventional manner and sensitized according to the same procedure as in preparation of the above sensitized emulsion A but separately with the use of half amounts of sensitizers and stabilizers to prepare a sensitized emulsion B. The emulsions A and B Layer - 2...Medium sensitivity silver halide emulsion To 1 kg of an emulsion prepared by mixing the emulsion A and the emulsion B as shown in Layer - 1 was added 200 ml of the dispersion (M - 3) to prepare a medium sensitivity silver halide emulsion, which was then coated to a dry film thickness of 1.5μ.

Layer - 3...Intermediate layer

An aqueous gelatin solution was applied to a dry film thickness of 1.0μ.

Layer - 4...High sensitivity green-sensitive silver halide emulsion layer

A silver iodobromide containing 7 mole % of silver iodide (average grain size 0.9μ, containing 0.25 mole of silver halide and 30 g of gelatin per 1 kg of emulsion) was prepared in a conventional manner and 1 kg of this emulsion was chemically sensitized with gold and sulfur sensitizers, and further mixed with, as green sensitive sensitizing dyes, anhydrous 5,5'-dichloro-9-ethyl-3,3'-di-(3-sulfopropyl)oxacarbocyanine hydroxide; anhydrous 5,5'-diphenyl-9-ethyl-3,3'-di-(3-sulfopropyl)oxacarbo-cyanine hydroxide; and anhydrous 9-ethyl-3,3-di-(3-sulfopropyl)-5,6,5', 6'-dibenzoxacarbocyanine hydroxide, followed by addition of 0.25 g of 4-hydroxy-6-methyl-1,3,3a,7-tetrazaindene, 5 mg of 1-phenyl-5-mercaptotetrazole, 0.2 g of polyvinyl pyrrolidone. Then, to the resultant mixture was added 200 ml of the above dispersion (M-2) to prepare a high sensitivity green-sensitive silver halide emulsion, which was then applied to a dry film thickness of 2.0μ.

Layer - 5...Yellow filter layer (the same as Layer - 4 in Sample - 1 in Example 1)

Sample - 8

Layer - 1...Low sensitivity green-sensitive silver halide emulsion layer (the same as Layer -1 in Sample - 7 in Example 2)

Layer - 2...Medium sensitivity green-sensitive silver halide emulsion layer (the same as Layer -2 in Sample - 7 in Example 2)

Layer - 3...Intermediate layer (the same as Layer - 2 in Sample - 5 in Example 1)

Layer - 4...High sensitivity green-sensitive silver halide emulsion layer (the same as Layer -4 in Sample - 7 in Example 2)
Layer - 5...Yellow filter layer (the same as Layer - 4 in Sample - 7 in Example 1)

Sample - 9

Layer - 1...Low sensitivity green-sensitive silver halide emulsion layer (the same as Layer -1 in Sample - 7 in Example 2)
Layer - 2...Intermediate layer (the same as Layer - 2 in Sample - 5 in Example 1)
Layer - 3...Medium sensitivity green-sensitive silver halide emulsion layer (the same as Layer -2 in Sample - 7 in Example 2)
Layer - 4...High sensitivity green-sensitive silver halide emulsion layer (the same as Layer -4 in Sample - 7 in Example 2)
Layer - 5...Yellow filter layer (the same as layer - 4 in Sample - 1 in Example 1)

The Samples thus prepared were processed similarly as in Example 1 and evaluated for graininess and sharpness of the green-sensitive layers. As the result, as compared with Samples 7 and 9 for comparative purpose, the Sample 8 of this invention was found to exhibit the effect of this invention similarly as in Example 1, particularly marked improvement at the leg portion graininess.

EXAMPLE 3

On a support of a cellulose triacetate layer applied with subbing treatment, the respective layers as shown below were provided by coating successively from the support side to prepare Samples 10 through 15.

Sample - 10

Same as Sample - 1 in Example 1

Sample - 11

Same as Sample - 2 in Example 1

Sample - 12

Except for adding the dispersion (X - 1) shown below in place of the dispersion (AS) used in Layer - 2 in the above Sample - 11, the procedure in preparation of Sample - 11 was followed to prepare Sample - 3.

Sample - 13

Except for adding the dispersion (C - 1) shown below in place of the dispersion (AS) used in Layer - 2 in the above Sample - 11, the procedure in preparation of Sample - 11 was followed to prepare Sample - 4.

Sample - 14

Except for adding the dispersion (Y - 1) shown below in place of the dispersion (AS) used in Layer - 2 in the above Sample - 11, the procedure in preparation of Sample - 11 was followed to prepare Sample - 5.

Sample - 15

Layer - 1...Low sensitivity green-sensitive emulsion layer
  Same as Layer - 1 in Sample - 1 in Example 1.
Layer - 2...Intermediate layer
  Layer - 2 in Sample - 1 in Example - 1 was applied to a dry thickness of 0.5μ.
Layer - 3...Intermediate layer
  Same as Layer - 2 in Sample - 14.
Layer - 4...Intermediate layer
  Same as Layer - 2 in Sample - 14.
Layer - 5...High sensitivity green-sensitive emulsion layer
  Same as Layer - 3 in Sample - 1 in Example 1
Layer - 6...Yellow filter layer
  Same as Layer - 4 in Sample - 1 in Example 1

The dispersions employed in the respective emulsion layers and intermediate layers were prepared as follows.

Dispersion (X - 1):
A solution of 60 g of the Example compound [VII - 9] of this invention dissolved in a mixture of 60 g of TPC and 180 ml of EA was added into 500 ml of 7.5 % gelatin solution containing 8 g of sodium triisopropylnaphthalene sulfonate and emulsified in a colloid mill, followed by make-up to 1,000 ml.

Dispersion (C - 1):
Except for using the Example compound [VII - 22] of this invention in place of the Example compound [VII - 9] of this invention, emulsification and make-up were conducted similarly as in preparation of the above Dispersion (X -1).

Dispersion (Y - 1):
Except for using the Example compound [VII - 2] of this invention in place of the Example compound [VII - 9] of this invention, emulsification and make-up were conducted similarly as in preparation of the above Dispersion (X -1).

After having given white light exposure on these Samples through an optical wedge, processing was performed, following the same processing steps as in Example 1, except for changing the composition of fixing solution as follows.

| [Composition of fixing solution] | |
|---|---|
| Ammonium thiosulfate | 175.0 g |
| Anhydrous sodium sulfite | 8.6 g |
| Sodium metasulfite | 2.3 g |
| Made up to one liter with addition of water and adjusted to pH 6.0 with acetic acid. | |

Subsequently, for the color images formed on the above respective Samples, the results on the same day of fog, sensitivity and gamma, and the results thereof after storage for 3 days under the conditions of 55° C., 10% relative humidity were measured similarly as in Example 1. These results are given in Table 2.

TABLE 2

| Sample No. | On the same day | | | Storability | | | Graininess (RMS) | | Sharpness (MTF) | |
|---|---|---|---|---|---|---|---|---|---|---|
| | Fog | Sensitivity | Gamma | Fog | Sensitivity | Gamma | Fog + 0.1 | Fog + 0.4 | 10/mm | 30/mm |
| 10 (Comparative) | 0.13 | 100 | 0.57 | 0.13 | 100 | 0.56 | 32 | 45 | 90 | 37 |
| 11 (Comparative) | 0.13 | 98 | 0.58 | 0.16 | 85 | 0.65 | 29 | 40 | 95 | 45 |

TABLE 2-continued

| Sample No. | On the same day | | | Storability | | | Graininess (RMS) | | Sharpness (MTF) | |
|---|---|---|---|---|---|---|---|---|---|---|
| | Fog | Sensitivity | Gamma | Fog | Sensitivity | Gamma | Fog + 0.1 | Fog + 0.4 | 10/mm | 30/mm |
| 12 (This invention) | 0.12 | 100 | 0.57 | 0.13 | 100 | 0.57 | 22 | 29 | 95 | 48 |
| 13 (This invention) | 0.13 | 100 | 0.58 | 0.14 | 100 | 0.58 | 18 | 25 | 97 | 50 |
| 14 (This invention) | 0.12 | 100 | 0.58 | 0.13 | 100 | 0.59 | 19 | 26 | 97 | 50 |
| 15 (This invention) | 0.12 | 100 | 0.58 | 0.12 | 100 | 0.57 | 18 | 26 | 95 | 44 |

As apparently seen from the results in the above Table 2, Samples 12, 13, 14 and 15 according to this invention, as compared with Samples 10 and 11 outside the scope of the present invention, exhibited excellent characteristics in all of storability, graininess and sharpness. In particular, improvement in graininess is marked, which should be appreciated to be a surprising effect surpassing to a great extent the result expected from the system employing the dispersion (AS).

EXAMPLE 4

On a support of a cellulose triacetate layer applied with subbing treatment, the respective layers as shown below were provided by coating successively from the support side to prepare Samples 16, 17 and 18.

Sample - 16

Layer - 1. . .Low sensitivity green-sensitive emulsion layer
Same as Layer - 1 in Sample - 7 in Example 2
Layer - 2. . .Medium sensitivity emulsion layer
To 1 Kg of a mixture of the emulsion A and the emulsion B at a ratio of 1:1 as shown in Layer - 1 in Example 2 was added 200 ml of the above dispersion (X - 1) to prepare a medium sensitivity emulsion (2), which was applied to a dry film thickness of 1.5μ.
Layer - 3. . .Intermediate layer
Same as Layer - 3 in Sample - 7 in Example 2
Layer - 4. . .High sensitivity green-sensitive emulsion layer
Same as Layer - 4 in Sample - 7 in Example 2
Layer - 5. . .Yellow filter layer
Same as Layer - 4 in Sample - 10 in Example 3.

Sample - 17

Layer - 1. . .Low sensitivity green-sensitive emulsion layer
Same as Layer - 1 in Sample - 16
Layer - 2. . .Medium sensitivity green-sensitive emulsion layer
Same as Layer - 2 in Sample - 16
Layer - 3. . .Intermediate layer
Same as Layer - 2 in Sample - 14 in Example 3
Layer - 4. . .High sensitivity green-sensitive emulsion layer
Same as Layer - 4 in Sample - 16
Layer - 5. . .Yellow filter layer
Same as Layer - 4 in Sample - 10 in Example 3

Sample - 18

Layer - 1. . .Low sensitivity green-sensitive emulsion layer
Same as Layer - 1 in Sample - 16
Layer - 2. . .Intermediate layer
Same as Layer - 2 in Sample - 14 in Example 3
Layer - 3. . .Medium sensitivity green-sensitive emulsion layer
Same as Layer - 2 in Sample - 16
Layer - 4. . .High sensitivity green-sensitive emulsion layer
Same as Layer - 4 in Sample - 16
Layer - 5. . .Yellow filter layer
Same as Layer - 4 in Sample - 10 in Example 3

The Samples thus prepared were processed similarly as in Example 3 and evaluated for graininess and sharpness of the green-sensitive layers. As the result, as compared with Samples - 16 and 18 for comparative purpose, the Sample - 17 of this invention was found to exhibit the effect of this invention similarly as in Example 3, particularly marked improvement at the leg portion graininess.

We claim:

1. A light-sensitive silver halide photographic material having at least one light-sensitive layer constituted of a plural number of silver halide emulsions which are substantially the same in color sensitiveness but different in light sensitivity and containing a diffusion resistant coupler for photography capable of forming a diffusion resistant color forming dye through the reaction with the oxidized product of a color developing agent provided on a support, which comprises a non-light-sensitive intermediate layer provided at least adjacent to the silver halide emulsion layer with the highest light sensitivity among said plural number of silver halide emulsion layers on its support side, said non-light-sensitive intermediate layer containing a diffusion resistant coupler capable of forming a migratable color forming dye which can be color formed to substantially the same hue as the said diffusion resistant color forming dye through the coupling reaction with the oxidized product of a color developing agent or a compound capable of forming a flow-out type coupling product through the coupling reaction with the oxidized product of a color developing agent.

2. A light-sensitive silver halide photographic material according to claim 1, wherein the diffusion resistant coupler is represented by the following formula [I]:

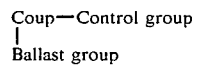

[I]

wherein Coup is a coupler mother nucleus capable of forming a color forming dye through the coupling reaction with the oxidized product of a color developing agent; Ballast group is a group which is bonded to the coupling position of said coupler and can be eliminated from Coup during the coupling reaction between said coupler and the oxidized product of a color developing agent, said Ballast such that the coupler is non-diffusive; and Control group is a group bonded to Coup at the non-coupling position for controlling the color forming dye formed through the coupling reaction between the coupler and the oxidized product of a color developing agent so that it may be mobile.

3. A light-sensitive silver halide photographic material according to claim 2, wherein the diffusion resistant coupler is contained in the intermediate layer in an amount of $1 \times 10^{-7}$ mole/m$^2$ to $8 \times 10^{-4}$ mole/m$^2$.

4. A light-sensitive silver halide photographic material according to claim 2, wherein the diffusion resistant coupler is a yellow coupler represented by the following formula [II]:

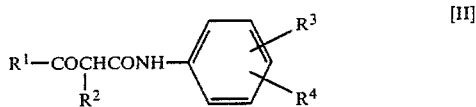

wherein $R^1$ is an aryl group or an alkyl group; $R^2$ is the ballast group as defined above; $R^3$ is the control group; and $R^4$ is a hydrogen atom, a halogen atom, an alkyl group, an alkoxy group or the control group as defined above.

5. A light-sensitive silver halide photographic material according to claim 2, wherein the diffusion resistant coupler is a cyan coupler represented by the following formula [III] or [IV]:

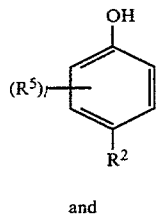

and

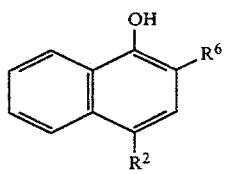

wherein $R^2$ is the ballast group as defined above; at least one of $R^5$ is the control group as defined above, and the remainder representing either identical or different hydrogen atoms, halogen atoms, alkyl groups, alkoxy groups, alkylamino groups or acylamide groups; l is an integer of 1 to 3; and $R^6$ represents the control group as defined above.

6. A light-sensitive silver halide photographic material according to claim 2, wherein the diffusion resistant coupler is a magenta coupler represented by the following formula [V] or [VI]:

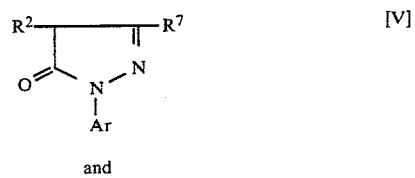

and

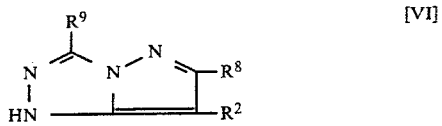

wherein $R^2$ is the ballast group as defined above; $R^7$ represents the control group as defined above; Ar is a phenyl group which may have at least one of a substituent selected from the group consisting of a halogen atom, an alkyl group, an alkoxy group and an amino group, and said phenyl group may have the control group; one of $R^8$ and $R^9$ represents the control group and the other represents a hydrogen atom, halogen atom, alkyl group, alkoxy group, aryl group, amino group or acylamide group.

7. A light-sensitive silver halide photographic material according to claim 1, wherein the compound capable of forming a flow-out type coupling product is represented by the following formula [VII]:

$$\underset{\underset{\text{BALL}}{|}}{\text{COUP}}\text{—SOL} \qquad \text{[VII]}$$

wherein COUP is a coupler mother nucleus having a coupling site (asterisk *); BALL is a group which is bonded to the coupling site of COUP and can be eliminated from COUP during the reaction between said COUP and the oxidized product of a color developing agent, said BALL being a Ballast group having a size and a shape such that the compound of the formula [VII] is diffusion resistant; and SOL is a solubilizing group, which is bonded to COUP at the non-coupling position and imparts mobility to the coupling product formed by coupling between COUP and the oxidized product of a color developing agent so as to be flown out of the system from within the light-sensitive material during or after color developing processing.

8. A light-sensitive silver halide photographic material according to claim 7, wherein the compound capable of forming a flow-out type coupling product is contained in the intermediate layer in an amount of $1 \times 10^{-7}$ mole/m$^2$ to $8 \times 10^{-4}$ mole/m$^2$.

9. A light-sensitive silver halide photographic material according to claim 7, wherein the compounds capable of forming a flow-out type coupling product is a yellow dye forming compound represented by the following formula [VIII]:

$$R^{10}-\underset{\underset{R^{11}}{|}}{\text{COCHCONH}}-\text{[VIII]}$$

wherein $R^{10}$ is an aryl group or an alkyl group; $R^{11}$ is the ballast group as defined above (BALL); $R^{12}$ is the control group or the solubilizing group (SOL) as defined above; $R^{13}$ is a hydrogen atom, a halogen atom, an alkyl group or an alkoxy group; and n and m are integers satisfing the relation of n+m=5 provided that each n and m are not zero, and when n and m are 2 or more, the plural groups may be either identical or different.

10. A light-sensitive silver halide photographic material according to claim 7, wherein the compound capable of forming a flow-out type coupling product is a cyan dye forming compound represented by the following formula [IX] or [X]:

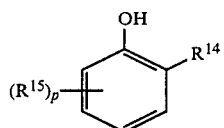

and

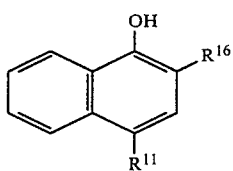

wherein $R^{11}$ is the ballast group (BALL) as defined above; at least one of $R^{14}$ and $R^{15}$ is the solubilizing group (SOL) as defined above, and the remainder representing either identical or different hydrogen atoms, halogen atoms, alkyl groups, alkoxy groups or alkylamide groups; p is an integer of 1 to 3; and $R^{16}$ represents the solubiliaing group (SOL) as defined above.

11. A light-sensitive silver halide photographic material according to claim 7, wherein the compound capable of forming a flow-out type coupling product is a magenta dye forming compound represented by the following formula [XI] or [XII]:

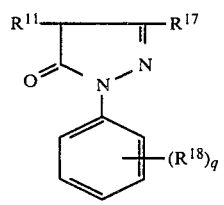

and

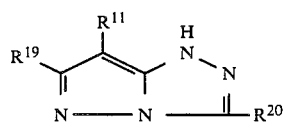

wherein $R^{11}$ is the ballast group (BALL) as defined above; $R^{17}$ represents the solubilizing group (SOL) as defined above; $R^{18}$ represents a hydrogen atom, a halogen atom, an alkyl group, an alkoxy group or an amino group; q is an integer of 1 to 5 provided that when q is 2 or more, the plural groups may be either idential or different; and one of $R^{19}$ and $R^{20}$ represents the solubilizing group (SOL) as defined above and the other represents a hydrogen atom, an alkyl group, an alkoxy group, an aryl group or an amino group.

12. A light-sensitive silver halide photographic material according to claim 2, wherein the Control group is an alkyl group having 1 to 20 carbon atoms and an aryl group having 6 to 20 carbon atoms.

13. A light-sensitive silver halide photographic material according to claim 12, wherein the Control group is further connected with a divalent group selected from the group consisting of —O—, —S—, —CO—, —COO—, —NR—, —CONR—, —NRCO—, —SO$_2$NR—, —NRSO$_2$—and —NRCONR— wherein R is a hydrogen atom, an alkyl group or an aryl group.

14. A light-sensitive silver halide photographic material according to claim 2, wherein the Ballast group is an alkyl group or an aryl group having 8 to 32 carbon atoms.

15. A light-sensitive silver halide photographic material according to claim 14, wherein the Ballast group is further connected with a divalent group selected from the group consisting of —O—, —S—, —N=N—and

wherein Z is a group of atoms necessary for forming a 5- to 7-membered heterocyclic ring.

16. A light-sensitive silver halide photographic material according to claim 7, wherein the SOL is a group selected from the group consisting of an ionizable hydroxyl group, carboxyl group, sulfo group and aminosulfonyl group and ionizable salts thereof or a group having these group.

17. A light-sensitive silver halide photographic material according to claim 7, wherein the SOL is a group of an alkyl group having 1 to 10 carbon atoms or an aryl group having 6 to 12 carbon atoms containing one or two or more hydroxyl group, sulfo group or ionizable salt thereof.

18. A light-sensitive silver halide photographic material according to claim 17, wherein the SOL is further connected with a divalent group selected from the group consisting of an oxy (—O—), thio (—S—), carbonyl group, carboxyl group, oxycarbonyl group, amino group, carbamoyl group, aminocarbonyl group, ureido group, sulfamoyl group and aminosulfonyl group.

19. A light-sensitive silver halide photographic material according to claim 17, wherein the SOL is further connected with an amino group and/or a carbonyl group.

20. A light-sensitive silver halide photographic material according to claim 7, wherein the BALL is an alkyl group or an aryl group having 8 to 32 carbon atoms.

21. A light-sensitive silver halide photographic material according to claim 20, wherein the BALL is further connected with a divalent group selected from the group consisting of —O—, —S—, —N=N—and

wherein Z is a group of atoms necessary for forming a 5- to 7-membered heterocyclic ring.

* * * * *